(12) United States Patent
Reier

(10) Patent No.: US 9,727,885 B1
(45) Date of Patent: Aug. 8, 2017

(54) SYSTEMS AND METHODS FOR PRODUCING PERSONALIZED HEALTH RECOMMENDATION DATA

(71) Applicant: Benovate Inc., Minneapolis, MN (US)

(72) Inventor: Mike Reier, Minneapolis, MN (US)

(73) Assignee: Benovate Inc., Minneapolis, MN (US)

( * ) Notice: Subject to any disclaimer, the term of this patent is extended or adjusted under 35 U.S.C. 154(b) by 433 days.

(21) Appl. No.: 13/906,760

(22) Filed: May 31, 2013

Related U.S. Application Data

(63) Continuation of application No. 13/831,294, filed on Mar. 14, 2013, now abandoned.

(60) Provisional application No. 61/670,714, filed on Jul. 12, 2012.

(51) Int. Cl.
   *G06Q 50/22* (2012.01)
   *G06Q 30/02* (2012.01)

(52) U.S. Cl.
   CPC ......... *G06Q 30/0207* (2013.01); *G06Q 50/22* (2013.01)

(58) Field of Classification Search
   CPC ...... G06F 19/363; G06F 19/345; G06Q 50/22
   USPC ...................................................... 705/2–3
   See application file for complete search history.

(56) References Cited

U.S. PATENT DOCUMENTS

| | | | |
|---|---|---|---|
| 2007/0050215 A1* | 3/2007 | Kil ........................ | A61K 49/00 705/3 |
| 2007/0122780 A1* | 5/2007 | Moon ...................... | G09B 5/00 434/236 |
| 2008/0262866 A1* | 10/2008 | Greene ................. | G06Q 10/087 705/2 |
| 2012/0313776 A1* | 12/2012 | Utter, II ............... | A61B 5/0205 340/539.12 |

OTHER PUBLICATIONS

Intelliprev, "", http://www.intelliprev.com/homepage.htm.
Intelliprev, "Intelliprev Homepage", http://www.intelliprev.com/homepage.htm.
Intelliprev, "Intelliprev: A primer", http://organizationalwellness.com/wp-content/uploads/2013/02/1.IntelliPrevT_Primer.pdf.
Intelliprev, "Prevention Program Library (Overview) Introductory Research Note (1/3)", http://www.intelliprev.com/library_overview.cfm?sc=0.
Intelliprev, "Prevention Program Library (Overview) Introductory Research Note (2/3)", http://www.intelliprev.com/library_overview.cfm?sc=0.

(Continued)

*Primary Examiner* — Joy Chng
(74) *Attorney, Agent, or Firm* — Schwegman Lundberg & Woessner, P.A.

(57) ABSTRACT

Disclosed in some examples is a method including the operations of receiving responses for a plurality of assessments for an individual, the responses including responses for assessments of at least one physical and at least one psychological component of the individual's wellness; calculating numerical indicators for a plurality of wellness components for the individual based on the plurality of responses; determine at least one set of rules based upon an organization that the individual is associated with; determine a wellness recommendation based upon the set of rules and the numerical indicators; and presenting the wellness recommendation to the individual.

24 Claims, 16 Drawing Sheets

(56) References Cited

OTHER PUBLICATIONS

Intelliprev, "Prevention Program Library (Overview) Introductory Research Note (3/3)", http://www.intelliprev.com/library_overview.cfm?sc=0.
US Health Center, Inc., "Health Management Programs—Science and Technology", http://ushcinc.com/science-technology.html (last visited Nov. 26, 2013).
US Health Center, Inc., "Homepage", http://ushcinc.com last visited (Nov. 26, 2013).
US Health Center, Inc., "Personal Health Management—Products and Services", http://ushcinc.com/PHM-services.html last visited (Nov. 26, 2013).

* cited by examiner

| PERSONAL STRESS SURVEY | HEALTH EVENT RATING | | | | | MULTIPLIER | HEALTH FOCUS INITIATIVE | | | | |
|---|---|---|---|---|---|---|---|---|---|---|---|
| | 1 | 2 | 3 | 4 | 5 | | Budget | Debt | Savings | Investing | Retirement/Legacy |
| What is your household income? | Free Text Data Point | | | | | | | | | | |
| I have a lot of stress around paying my monthly bills. | Strongly Disagree | Disagree | Between | Agree | Strongly Agree | xx.xx | 22 | | | | |
| I need the following to pay my bills and save 20% of my income. | 40% more | 20% more | I have enough | 20% less | 40% less | xx.xx | -10 | | | | |
| How much do you have saved for an emergency? | Free Text Data Point | | | | | | | | | | |
| How many months could you survive without income? | 6 months | 3 months | 2 months | 1 month | none | | | | | | |
| In how many years do you want to retire? | 30+ | 20+ | 15+ | 10+ | <5 | | | | | | |
| How much money do have saved for retirement? | Free Text Data Point | | | | | | | | | | |
| At retirement what standard of living are you planning on living? | much less | less | same | higher | much higher | | | | | | |
| Do you want your children to go to college? | No | if its affordable | yes | it's a priority | its required | | | | | | |
| I am very concerned about saving money | Strongly Disagree | Disagree | Between | Agree | Strongly Agree | | | | | | |

*FIG. 11A*

| PERSONAL STRESS SURVEY | HEALTH EVENT RATING | | | | | MULTIPLIER | HEALTH FOCUS INITIATIVE | | | | |
|---|---|---|---|---|---|---|---|---|---|---|---|
| | 1 | 2 | 3 | 4 | 5 | | Budget | Debt | Savings | Investing | Retirement/Legacy |
| I pay my bills consistently on the same day each month | Strongly Disagree | Disagree | Between | Agree | Strongly Agree | xx.xx | -27 | | | | |
| I do a personal budget for me and/or my family each | <3 months | <6 months | <12 months | < 2 years | Never | xx.xx | 34 | | | | |
| I meet with my financial planner every | 2+ years | 12 months | 6 months | 3 months | Never | | | | | | |
| I update my will or death plan every | 2+ years | 12 months | 6 months | 3 months | Never | | | | | | |
| I have enough saved of life insurance to support my family or loved ones for the following time period | 30+ | 20+ | 15+ | 10+ | <5 | | | | | | |
| If I am disabled my standard of living will be | much less | less | same | higher | much higher | | | | | | |
| I am concerned about my loved ones ability to survive financially without my income | Strongly Disagree | Disagree | Between | Agree | Strongly Agree | | | | | | |
| I am very concerned about my ability to retire | Strongly Disagree | Disagree | Between | Agree | Strongly Agree | | | | | | |
| I have the ability to manage my finances on my own | Strongly Disagree | Disagree | Between | Agree | Strongly Agree | | | | | | |
| I have a plan for where I will live when I am older | Strongly Disagree | Disagree | Between | Agree | Strongly Agree | | | | | | |

RESULTING FINANCIAL HEALTH SCORE 13      FINANCIAL HEALTH STATE : AT RISK

*FIG. 11B* benovate
Health Risk Scoring

| | Health Priority |
|---|---|
| Resulting Financial Health Stress Score: 13 | 1 |
| Financial (Money) Risk State: At Risk | |
| Resulting Relationship Stress Score: 32 | 2 |
| Resulting Relationship (People) Risk State: Healthy | |
| Resulting Career Stress Score: 37 | 3 |
| Career (Job) Risk State: Healthy | |
| Resulting Health Stress Score: 70.1 | 4 |
| Health Risk State: Healthy | |

*FIG. 12*

SYSTEMS AND METHODS FOR PRODUCING PERSONALIZED HEALTH RECOMMENDATION DATA

CLAIM OF PRIORITY

This patent application is a continuation application of and claims the benefit of priority to U.S. patent application Ser. No. 13/831,294, filed on Mar. 14, 2013, which claims the benefit of priority, under 35 U.S.C. Section 119(e), to U.S. Provisional Patent Application Ser. No. 61/670,714, entitled "Benovate," filed on Jul. 12, 2012 to Mike Reier, which is hereby incorporated by reference herein in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Benovate, All Rights Reserved.

BACKGROUND

Healthcare includes diagnosis and treatment of illness and injury. Many sponsors (e.g., companies or employers) provide healthcare to participants (e.g., employees) by subsidizing employee health plans or health insurance. Healthcare and health insurance have become increasingly expensive for both employers and employees.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 11A and B shows a diagram of a personal stress survey, associated wellness indicators, and a financial health stress score and financial health state.

FIG. 12 shows a diagram of a risk prioritization according to some examples of the present disclosure.

DETAILED DESCRIPTION

Figure 1:
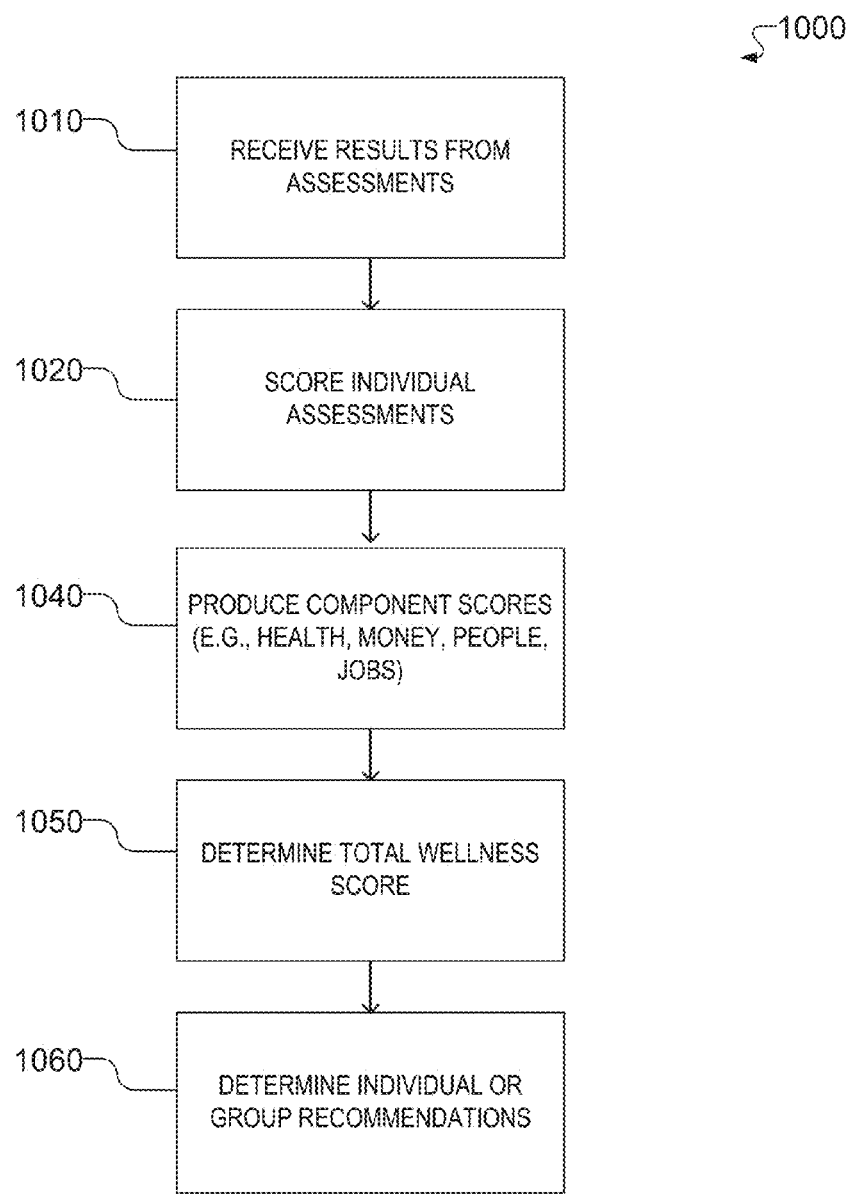
FIG. 1 shows a flowchart of a method for determining health recommendations according to some examples of the present disclosure.

Healthcare currently functions in a reactive capacity, focusing on treating sickness instead of promoting health, thereby potentially wasting resources. Insurance carriers provide products that are reactive, typically only used to pay for healthcare used to treat sickness that is already present. Healthcare distribution is similarly inefficient, where health insurance is sold by insurance brokers that receive the majority of their revenue from the medical insurance carriers. Because insurance brokers, insurance carriers, and medical institutions are reimbursed disproportionately to treat sickness, there is very little incentive to have a healthy population.

Traditional wellness programs have attempted to address this issue, for example, by providing economic incentives to all program participants for engaging in healthy behavior. These programs attempt to be a "one size" fits all solution where everyone is rewarded the same amount for engaging in the same health-promoting behaviors regardless of the individual's needs. By providing economic incentives to plan participants who pose a low risk of a costly health event, traditional wellness programs have proved inefficient. Additionally, traditional wellness programs may be difficult or cost-prohibitive for employers to manage and the benefit structures of traditional wellness programs are perceived by employers not as an investment, but as an expensive burden. For example, if a company already has a health insurance benefit program, adding a traditional wellness program can seem redundant with the health insurance benefit program, especially if the wellness program does not have a demonstrable return-on-investment. Similarly, many employees have found the benefit structure to be confusing, difficult to learn and maintain, expensive, or addressing an issue unrelated to the employees' needs. Wellness programs have also failed to address the underlying psychological component of why individuals may not take proactive steps to improve their health.

Disclosed in some examples are systems, methods, and machine-readable media for providing specific and personalized recommended activities for a participant based on their specific profiles to improve their health. The system may recommend activities based upon evidence based perspectives and an individual's health profile that will increase their overall health. This system recognizes that stress factors such as organizational and cultural stresses, family stresses, and financial stresses prevent individuals from taking action to be more healthy. For example, a particular person may be less stressed out about heavy financial debt load as they are about not having a life insurance policy. The system may identify this as a stress factor and recommend a life insurance policy. This system thus provides a customized solution that is lacking in traditional wellness systems.

In some examples, this enables individuals to identify and actively manage their individual health risks, and thereby use preventative measures to avoid costly, reactive healthcare measures. This approach may expand the definition of health to include components of stress management, life solutions, managed health solutions, and improved work-life balance. By determining what people actually need based on their family's specific situation, this approach avoids inefficiencies inherent in traditional wellness programs, which focus on healthy lifestyle programs as a "one size fits all" solution.

To provide this personalized health data, participants may take one or more surveys. In some examples, a participant may take a plurality of surveys each focused on a different level of their lives. For example, a participant may take a culture and climate survey (e.g., related to their jobs), a relationship and family survey (e.g., their relationships or family stresses), and a personal stress survey (which may focus on money stress and health related stress). One of ordinary skill in the art with the benefit of applicants' disclosure will appreciate that other surveys focusing on different levels of a participant's life may be utilized.

These surveys may be scored to produce wellness indicators that describe how healthy a particular person is in a particular aspect of their life (e.g., their physical health, mental health, financial health, or the like). For example, a wellness indicator may include a triglyceride level, a body mass index, a credit score, a debt score, a relationship health score, or the like. The wellness indicator scores for each level may be aggregated across all the participants in that particular level to produce an aggregated score. For example, the culture and climate survey may be scored to produce health indicators and the health indicator scores may be aggregated with all other participants in the same culture and climate (e.g., the same industry). Similarly, the scores for the relationship and family survey may be aggregated across all other participants in the same relationship and family. The personal stress surveys are personal to the individual and may not be aggregated. To calculate this aggregation the system may take an average of all the participants' scores or use some other algorithm which may weight one or more of the participants' scores. These aggregate health indicator scores, along with the personal stress scores may be used for calculating a number of health component scores for each participant. Example health component scores may include a physical health component, a money stress component, a relationship stress component, and a job stress component. These component scores (and/or the health indicators) may then be used to calculate an aggregate health score. Based upon the health component scores and in some examples one or more of the groups the participant is associated with, the system may generate one or more predetermined recommendations which may be specifically designed to increase an individual's health. Rewards may be offered to participants for performing or following up on these personalized health recommendations. Rewards may include cash distributions (either in the form of an HRA contribution, cash payment, debit card, or the like). In this way, employers may incentivize evidence based healthy behaviors in employees, thus driving down overall healthcare costs.

Assessments

As already noted, the participants may be asked to take several surveys asking questions about the participant's life. Surveys may be grouped into three main categories: culture and climate survey, a personal stress survey, a personal health assessment and the like.

The culture and climate surveys may include questions about an individual's career-related health risks. For example, questions relating to the culture and climate of the individual's employer such as: current employer's industry, current perception of personal health, work-life balance, current level of engagement in personal health maintenance, ability to communicate within a team environment, workplace accountability and policy enforcement, workplace availability and use of stress coping mechanisms, and workplace availability of help and support. A number of wellness indicators may be determined from the culture and climate survey including a health and wellness indicator that indicates an overall status of physical health a work-life balance indicator indicating an amount of time spent at work versus non-work, a presence and engagement indicator measuring an ability to focus at work, a team communication indicator related to stress associated work with peers and supervisors, a policy and accountability indicator which indicates stress associated with the organization within a workplace, a coping with stress indicator which determines how much stress a person can manage internally, a help and support indicator that provides a measurement of existing support resources, and the like.

The personal stress surveys may include assessments of an individual's current relationships and family situation. Questions may include questions directed to whether an individual is single, divorced, or married. If an individual is single, additional questions may prompt the individual to describe whether they are dating, whether they are interested in meeting new people, or whether they are interested in marriage. If an individual is divorced, additional questions may prompt the individual to describe the issues that lead to the end of the marriage. If an individual is married, additional questions may prompt the individual to provide an assessment of the health of the marriage. Questions may inquire as to the number of children the individual currently as, whether the children are living at home, and whether the individual would like to have additional children. If an individual has children, additional questions may prompt the individual to provide a self-assessment of the effectiveness of the parent-child communication. If an individual has recently moved to a new city the questions are designed to determine the extent that a lack of known friendships in the new city are impacting the persons stress levels. A number of wellness indicators may be determined including stress factors related to unhealthy relationships, loneliness, and the like.

The personal stress surveys may also contain components directed at discovering sources of stress in an individual's life such as stress about finances or about their health. These surveys may include assessments of an individual's personal stress (e.g., money and health). Questions are directed around the sources of financial stress as well as actual financial status. A number of wellness indicators may be determined including stress factors related to maintaining a budget, personal or family savings, or retirement, with a goal of pinpointing what area would have the most dramatic impact on overall stress if it were managed in a better fashion.

The personal stress survey may also contain questions directed at an individual regarding their current employment, desired employment, or employment advancement. Questions may include questions about supervisor effectiveness, ability to grow, known career path, desired career path and the like. A number of wellness indicators may be determined, including current job satisfaction, desired job satisfaction, personal growth, potential and steps to achieve life goals.

The Personal Health Surveys may incorporate data from standardized biometrics assessments in order to determine the actual health state of the individual. These health factors are further weighted by known health criteria to be able to provide a reflection of the current physical health state. The laboratory provides health indicators related to tobacco use, BMI, body fat content, waist/hip ratio, blood pressure, glucose, total cholesterol, HDL, LDL, TC/HDL Ratio, Triglycerides, GGT, and CRP. The lab results are compared to normal values as part of scoring the health state of an individual.

Scoring

These surveys may then be scored based upon the participant's responses to the survey questions. These scores may provide a plurality of wellness indicators indicating a wellness with respect to an aspect of the participant's health and the activities they undertake related to improving or degrading their health. For example, wellness indicators may include a determined risk of heart disease, a cholesterol level, a family stress level, a personal stress level, a stress level related to job stress, a stress level related to family stress, or the like. The scores are determined by an evidenced based approach that has determined which stress mitigation activities are known to decrease a specific stress condition incorporated into a summary and within the context of known physical health data. The scores may also be determined by an evidenced approach that has determined which health improvement activities are known to have the impact on the specific health condition. For example: if the Personal Stress Survey indicated that a person has the highest stress rating about their ability to retire versus paying their existing bills, the activity related to facilitating retirement would have a higher score then setting up a daily budget. If retirement planning was not part of the determined routine, then that person would have a lower financial health score even if their physical health metrics remained the same. For example: if the Personal Health Survey indicates significantly elevated triglycerides in conjunction with other health data a specific diet known to lower the level of triglycerides would have the higher score, and if that diet was avoided or not undertaken it would result in a lower score. These scores may be a numerical score representing a level of concern with respect to that health indicator. The surveys may be scored by assigning a numerical point value for particular responses to particular questions that is assigned to particular indicators.

For example, the culture and climate survey may contain a question such as "how many hours do you spend at work a week?" followed by options of "0-20 21-30 31-40 41-50 50-60 60 or more." The survey may be scored by assigning the option of 0-20 to be 2 points, 21-30 to be 3 points, 41-50 to be 5 points, 50-60 to be 4 points and 60 or more to be 2 points. The wellness indicators may be calculated using a weighted sum of the scores for one or more survey questions. I.e., these points may be added (or subtracted if desired) from a number of wellness indicators (and weighted), such as a work-life balance indicator. In this example, an optimal score for an individual may be 5 points as it represents a healthy work life balance. Scoring may be more complicated in that scores may take into account previous answers. For example, if a previous question asks "do you feel underemployed?" and the participant answered "no," then the points may be adjusted such that a range of 0-20, 21-30 and 31-40 may be worth additional points as the person is apparently happy with working fewer hours.

Based on the survey scores, a number of aggregate wellness indicators for each aspect of the participant's life may be computed. For example, in the case of organizational culture and climate, the scores may be aggregated with other participant's scores in that organization. In the case of relationships and family, one or more members of a participant's family may be given the survey and the score may be aggregated amongst the members of the family who have taken the survey. Thus the aggregate results may reflect not only the participant's response to the surveys, but the groups that the participant is a part of as well (e.g., industry, company, family, etc. . . . ) to produce a more complete picture of that person's life. For example, the aggregate indicators may be calculated by using a weighted average across the wellness indicators of all participants in that group who have had their surveys scored.

As noted, the wellness indicators may then be used to calculate a number of health component scores summarizing an individual's wellness in key areas. For example: 1.) health 2.) money or financial stresses 3.) people or relationship stresses and 4.) job or career stresses. These four health components may be calculated based upon a weighted sum of one or more of the indicators calculated from the surveys. In the case of the climate and culture surveys and personal stress surveys, the calculations of the component scores may utilize the aggregate indicators or may use the individual's indicators. For example, a health score may be the weighted sum of the following indicators: adhering to a healthy diet on a daily basis, the most recent laboratory results for; triglycerides, BMI, Body Fat, or TC/HDL Ratio; days and hours per week exercised; or the number of visits to a nutritionist, personal trainer, or primary care physician. In another example, the money stresses score may be the weighted sum of the following indicators: daily budget management, paying within a specific budget for a specific meal, providing a certain dollar amount to a savings account, and meeting with a financial advisor. In some examples, the relationship stresses may be the weighted sum of the following indicators: hours spent at work, hours spent not at work, hours spent with friends, activities with families, meeting with a marriage counselor, or attending a networking event. In yet additional examples, the job stresses score may be the weighted sum of the following indicators: hours spent at work, level of satisfaction while at work, time spent in continuing education, developing a resume, meeting with a career counselor or attending an advanced training class.

A total wellness score may be calculated based upon the scores for the individual components. This total wellness score may be calculated based upon the weighted sums of the four components in combination with the known health conditions before engagement and the activities required to improve the specific health or stress condition Recommendations Next, recommendations for improving the health of an organization, a family, and an individual may be provided to employers, families, and employees. These recommendations may be personalized based upon industry, family, and individual. For example, each industry may have a number of predetermined rules which may specify the recommendations to give to a particular participant based upon their wellness indicators, the total wellness score, or a mix of both. For example, E.g., one example rule may be: if a participant's health score <40, or less than 32, and money score >35 then recommend a personal trainer. These rules may be determined by program administrators based upon clinical evidence.

Example recommendations may include exercising, scheduling a physical, scheduling a visit with a financial advisor, renewing a life insurance policy, assigning a health advocate, a health coach, a disease manager (if someone in your family is currently sick), fitness recommendations, nutrition recommendations, a budget manager, a debt manager, a legal manager, a financial planner, an insurance planner, a retirement director, a job counselor, education programs, career advancement programs, a relationships coach, marriage and family counselors, drug and addiction counselors, or the like. Similarly, the recommendations may also be provided on a departmental level. For example, if all of the scores within a particular department within a company are lower than industry average scores, then the company may receive a recommendation to investigate possible causes of the department's low scores. Recommended activities may be chosen from among a predetermined set of activities for each industry for example, a lower relationship score in a payroll department may indicate a manager that is in need of training.

Participant Engagement

In some examples, participants may be rewarded with direct economic incentives for engaging in various healthy activities (e.g., health-promoting activities) that boosts their total wellness score. Example rewards may include reductions in healthcare insurance costs. Alternatively, employees could receive credit-based economic rewards, such as through a system of "life management dollars" that can be used to pay for doctor visits or other health-promoting activities. This personalized health data could be used to shift economic incentives from equally rewarding all plan participants who remain healthy to rewarding plan participants for participating in personalized health-promoting activities.

The amount rewarded to a participant for an activity would depend on the specific recommendations and scores of a participant. Thus eating a salad might be worth more rewards to a person who is obese than to an individual who is a healthy weight. Thus, rather than a one size fits all approach, individuals are rewarded based upon activities clinically shown to improve their health.

Compliance with recommendations may be tracked in a number of ways. For example, a mobile application on a mobile device of a participant may track the user's location (e.g., through a Global Positioning System). If the system recommended a doctor visit, the mobile application could recommend a preventative visit to a doctor, and then provide a list of doctors that are available near the individual's home or office. The mobile device may then recognize that the participant's location matches that of a doctor's office. The system may then automatically note that the participant completed the recommendation and may automatically credit the user with the provided reward. In other examples, participants may self-report activities. In still other examples, health-care providers or other third parties may have a portal which may allow them to report the participant's participation in a recommended activity.

All this health data may be made accessible to participants through one or more engagement portals. For example, a desktop application, a mobile application, a web portal, or other user interface may be provided. The interface may deliver the assessments, receive the assessment answers from the participant, deliver health recommendations, deliver scoring results, deliver healthy tips (e.g., videos, personalized messages, or the like), or any other communication with the participant. These engagement portals may allow employees to focus on the products and services they need to meet their life goals and actively manage their health.

In some examples, the engagement portal may recognize that an individual is at the office for a long amount of time (e.g., using a global positioning system on a mobile device). Based upon a person's profile, the portal may recommend some activities to reduce stress based upon the fact that the user has been at the office for a long amount of time. For example, the engagement portal may recommend stretching exercises, a bike ride, or the like.

METHOD EXAMPLES

FIG. 1 shows a method 1000 for determining wellness recommendations according to some examples of the present disclosure. The method 1000 begins by receiving results (e.g., question answers) from assessments 1010 and scoring the individual assessments 1020 to produce wellness indicators. The assessments may include a series of questions allocated to various categories. The assessments may include culture and climate assessments, relationship and family assessments, personal stress level assessments, and the like. The questions of those assessments may be related to a list of known health conditions, whether the individual is taking medications or smokes, a self-assessment of diet, an approximate number of hours of exercise, and a self-assessment of work and home stress, whether the individual owns a home rental property, or one or more cars, hours spent at work each week, a self-assessment of personal net worth, and if the individual owns a business, how many employees the business employs, household income, how much money is currently saved for an immediate emergency, how many months the immediate emergency money would last if the individual or the individual's spouse lost their job, the age the individual wants to retire, how much money the individual has already saved for retirement, whether the individual wants to retire at a higher or lower standard of living, and whether the individual plans to pay for their children's college education.

The surveys may be scored to generate a set of wellness indicators. The indicators may be calculated based on a predetermined set of weights applied to a point value for an answer to a predetermined set of questions. For example, a question may include multiple answer options (e.g., strongly agree, agree, neutral, disagree, strongly disagree), where each answer choice is assigned a point score (e.g., 4, 3, 2, 1, 0, respectively). Each indicator may have a formula which determines which questions factor into the indicator and how much each question is weighted overall. Thus a work-life balance indicator may have a formula of $Q1*W1+Q2*W2$, where Q1 is the point value of question 1 (based on the participant's answers and the predetermined point values for each answer), W1 is the predetermined weight value of that question and Q2 is the point value of question 2, and W2 is the weight value of that question. In some examples, a survey question may require a yes or no answer, and the entire question may be weighted to assign a score. In some examples, a question with only two possible answers may be weighted to assign a point value that is a multiple of the point value for a multiple-choice question. For example, if "agree" is assigned four points, then "yes" might be assigned two, four, or eight points. Other point values may be used.

The score from a plurality of individual assessments 1020 from a particular industry, company, family, or any other group may be aggregated to produce scores for that particular group. The indicators for that group may then be used to produce the health component scores 1040, and a total wellness score 1050.

At operation 1040, component scores, such as a health score, a money (e.g., financial) score, a people score, and a jobs scores may be calculated. These scores may be calculated, for example, based upon a weighted sum of the survey scores (either aggregated survey scores in the case of the culture and climate surveys or the relationship and family survey or the individual survey scores for the personal stresses).

A health component score may be representative of a person's physical health. For example, someone who is sick may have a lower health score than a healthy individual. A health score may be reduced as an indication of the risk (e.g., uncertainty) associated with an individual's health. For example, a health score may be reduced if an individual cannot obtain health insurance for a dependent, if the individual avoids doctor visits because he or she does not know how to find or choose a doctor, or if the individual perceives his or her doctor is not helping.

A financial component score may be an indication of an individual's present financial state. For example, a financial score may be affected by income level, how much savings the individual has accrued, the current credit score of the individual, or the like. A financial score may be reduced as an indication of the risk (e.g., uncertainty) associated with an individual's financial stability. For example, a financial score may be reduced if individual's family does not have health insurance, or if the individual has a high debt-to-income ratio. In contrast, a financial score may also be increased if an individual demonstrates knowledge and familiarity with financial vehicles, including understanding what types of insurance are appropriate for the individual's family, or how to leverage a 401k or an IRA.

A relationship component (e.g., a people) score may be an indication of whether an individual's relationships tend to decrease stress or tend to increase stress. For example, an individual who has been married for twenty years may have a relationship score higher than an individual who is in the process of getting a divorce. A relationship score may be reduced as an indication of the risk (e.g., uncertainty) associated with an individual's relationship stability. For example, a relationship score may be reduced if the individual's daughter has an addiction problem, or if the individual has an elderly parent who is sick. In contrast, a relationship score may be increased if the individual indicates they participate regularly in social events with several close friends.

A career (e.g., jobs) component score may be an indication of an individual's current level of satisfaction with his or her career. For example, a person who has been working for the same employer for twenty years may have a career score higher than an individual who has worked at three different employers during the preceding three years. A career score may be reduced as an indication of the risk (e.g., uncertainty) associated with an individual's career stability. For example, a career score may be reduced if the individual loves his or her job but doesn't know how to get ahead, needs additional training, would like to become a supervisor, would like to move to a different department, or would like to go back to school.

The health component scores may then be used to calculate a total wellness score at operation 1050. In some examples, this score may be calculated based upon a weighted sum of the individual composite scores or may be calculated based upon one or more of the wellness indicators, or a combination of both.

Based on the composite scores and the overall score, recommendations may be generated for either the individual or the group at operation 1060. Recommendations may be generated by selecting one or more recommendations from a predetermined list of recommendations using one or more sets of rules. The predetermined list of recommendations may be customized based upon the participants industry, relationship status, company, group within that company, or any other social group with whom they are associated.

For example, the individual may be a trucker, a business manager, or a patent attorney. The recommendations provided may vary based upon this industry. An individual's industry may be determined directly by industry codes supplied by the employer, or an industry code may be selected by the employee from among a list of industries. In some examples, an industry may be inferred from survey results. For example, if an employee is a Senior Navigation Analyst working for Honeywell, the assessment may infer the employee works in the aerospace industry.

Each group for which the participant is associated (e.g., an industry they work in, a company they work for, a family they are a part of, or the like) may have a set of predetermined rules based upon empirical evidence that suggest activities to improve health based upon the indicators, the composite scores, or both. Thus, a truck driver's recommendations for poor health composite score might be to stop at a particular rest stop known for healthier food. The patent attorney recommendation for poor health might be to go on a bike ride. Each logical unit or group associated with the participant (e.g., industry, company, family, etc. . . . ) may have its own set of rules which provide recommendations based upon the indicators, the composite scores, or both. In some examples, when a participant is a member of multiple groups which offer different recommendations, another set of rules may govern which recommendation to offer. Thus if the system generates a first recommendation for truck drivers, and a second recommendation based upon that truck driver's family group, the rules may indicate that both recommendations may be presented to the participant in some examples. In other examples, the rules may resolve the conflicts of which recommendation to display.

Some example recommendations may include stopping to sleep at a rest stop during a particular time for a trucker (or when the trucker has been awake for a predetermined maximum time period). A recommendation for a business manager may include spending no more than twelve hours at the office. For example, a group recommendation may include recommending that all patent attorneys take a brief walk around their office building every two hours.

In addition to recommendations to a particular individual, recommendations may be generated for families as a whole, companies as a whole, or the like. For example, the predetermined rules may also provide recommendations to improve the scores of a company—such as dealing with a manager who is causing a lot of stress on employees under his or her supervision.

In some examples, the recommendations may be further subdivided (according to the predetermined rules) into different levels of risk within a particular group. For example, an industry may be divided into four groups based on the individual's scores. The top 20% of scores within the industry may be allocated to a first group, and recommendations for the first group may include activities to maintain their already excellent health. The next lower 30% of the scores may be allocated to a second group, and corresponding recommendations may include activities to promote current healthy habits and corrective activities specifically targeted at the health risks of the individual. The next lower 20% of the scores may be allocated to a third group, and corresponding recommendations may focus heavily on identifying and mitigating the causes of the health risks. The lowest 30% of the scores may be allocated to a fourth group, and corresponding recommendations may focus primarily on disease management. Each of these groups may have a set of predetermined rules to apply to create these recommendations.

To further illustrate the predetermined rules that determine the recommendations, consider the example of a married truck driver who works for ABC trucking and who is in a third health group. Truck drivers as an industry may have a set of rules for each health group. These rules may produce recommendations to the individual truck driver. ABC trucking may have a set of specialized rules for its employees for each health group. Again, these rules may produce recommendations for the individual truck driver. The truck driver himself may have personalized rules (created perhaps by a doctor or other professional) for his family for each health group that provide personal recommendations. To determine the recommendations presented to the truck driver, another set of rules may be used. Each set of rules may also have a number of predetermined rules which may provide recommendations to a manager or other head of a particular group on how to improve the overall group health (e.g., firing or reassigning a manager to improve performance of individuals under the manager's supervision).

Figure 2:
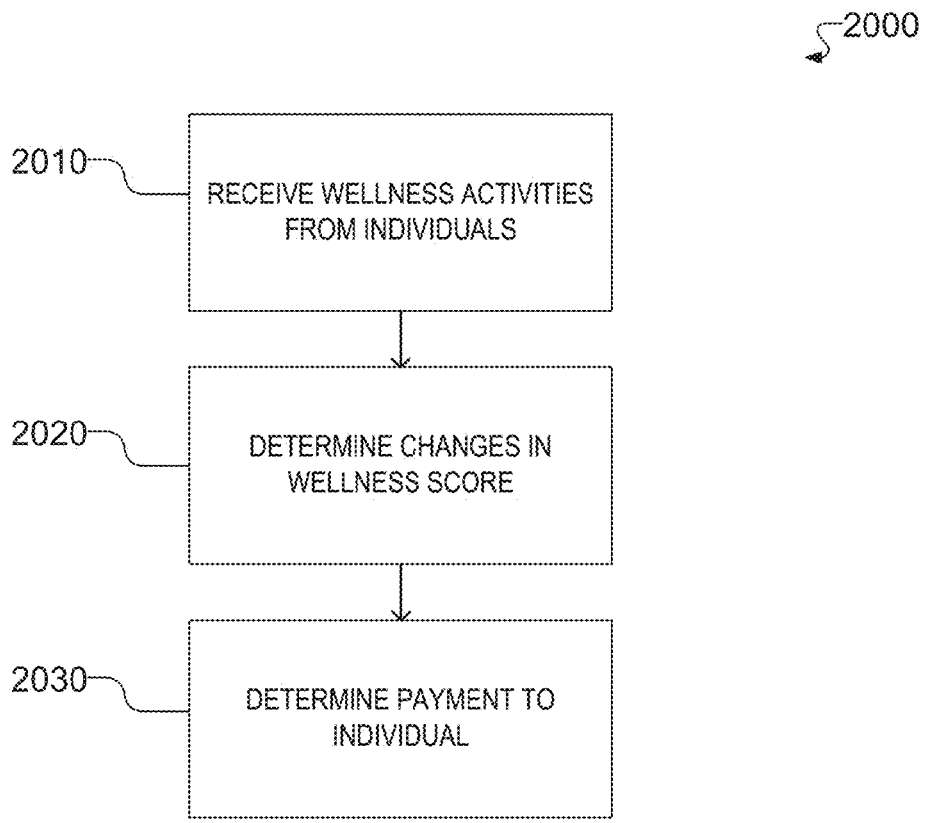
FIG. 2 shows a flowchart of a method for determining a wellness payment according to some examples of the present disclosure.

FIG. 2 shows a method 2000 of one form of participant engagement according to some examples of the present disclosure. The method 2000 includes receiving reports of wellness activities from individuals at 2010. For example, a wellness activity may include acting upon a recommendation, such as a trucker stopping to sleep at a rest stop. Reports of wellness activities may be automatically generated, such as through a mobile application that records a GPS location of a user, a motion of the user (e.g., walking, running, or jogging), or the like and compares them to known wellness activities and recommendations. In other examples, third parties may report activities. For example, a credit card may be linked to the participant's account and healthy purchases may automatically be recognized by the system and awarded points. In other examples, health insurance providers may report health-promoting activities of a participant.

Based on the individuals' previously determined wellness needs, the activities can be used to change the health component scores and the total wellness score of the individual 2020. For example, an individual may receive points (e.g., Work Life Balance points, or WLB points) for participating in healthy activities, and the points may be applied to increase an individual's total wellness score. The amount of points received for participating in healthy activities may be constant, such as receiving one point for each mile of a bicycle ride. The amount of points received for participating in healthy activities may vary based on the individual's health risk. For example, an individual may receive two points for each mile of a bicycle ride while the individual's weight is at or above two hundred pounds, and then receive one point for each mile of a bicycle ride while the individual's weight is below two hundred pounds. Various other factors may affect the number of points earned, the subjective health value of those activities, the effort applied to the activity, the weighted health value of those activities, the caloric value of the activity, the duration of the activity, the time the activity was undertaken, the amount of money that was spent to participate in the activity, or the outcome of the activity towards a designated health goal.

Points earned by an individual in a group may affect more than one health component. For example, a bicycle ride with family members may increase both a health component score and a relationship component score (as the family is spending quality time together). Thus for some activities, additional WLB points may be awarded.

Points awarded may be affected by the ratio of point accumulation to a pre-established goal and reward structure. For example, a wellness score may increase more at the beginning of the program and less after a period of time (e.g., one year after the beginning of the program). The predetermined rules used to recommend activities may also contain a database describing points to award based on activities and the distribution of those points across time. In addition, as already stated, recommended activities may change the wellness score more than non-recommended activities.

Based on the changes to the wellness score, a payment to an individual may be determined 2030. For example, if a health component score is increased, an individual may be credited an amount of money that may be applied to offset the cost of a preventative doctor visit. A summary report may be forwarded to an employer, where the report includes verified activities for inclusion in a calculation to determine an amount to be credited to an employee (e.g., as an HRA contribution, or the like). Additionally, the individual may be credited an amount that must be applied specifically toward a preventative doctor visit, and cannot be applied generally to a reactive doctor visit.

For example, the payout amount may be based on the impact to the wellness score. For example, a doctor visit may be worth X amount of points. A health impact factor may be chosen for this individual of Y (which indicates the expected impact of this activity on this individual user's health, or on the health of users in general). Based on the health impact factor, a weight value may be obtained. The score impact may be derived by multiplying X*Y*weight. Based on the wellness score impact, an employer multiplier may be chosen depending on the plan level of the employer or sponsor. For example, "Elite" employers may have a multiplier of 3, whereas "basic" employers may have a multiplier of 0.25. This multiplier may be multiplied by the score impact to produce a reimbursement amount. Thus, the reimbursement amount may be calculated based partially on the score impacts.

Figure 3:
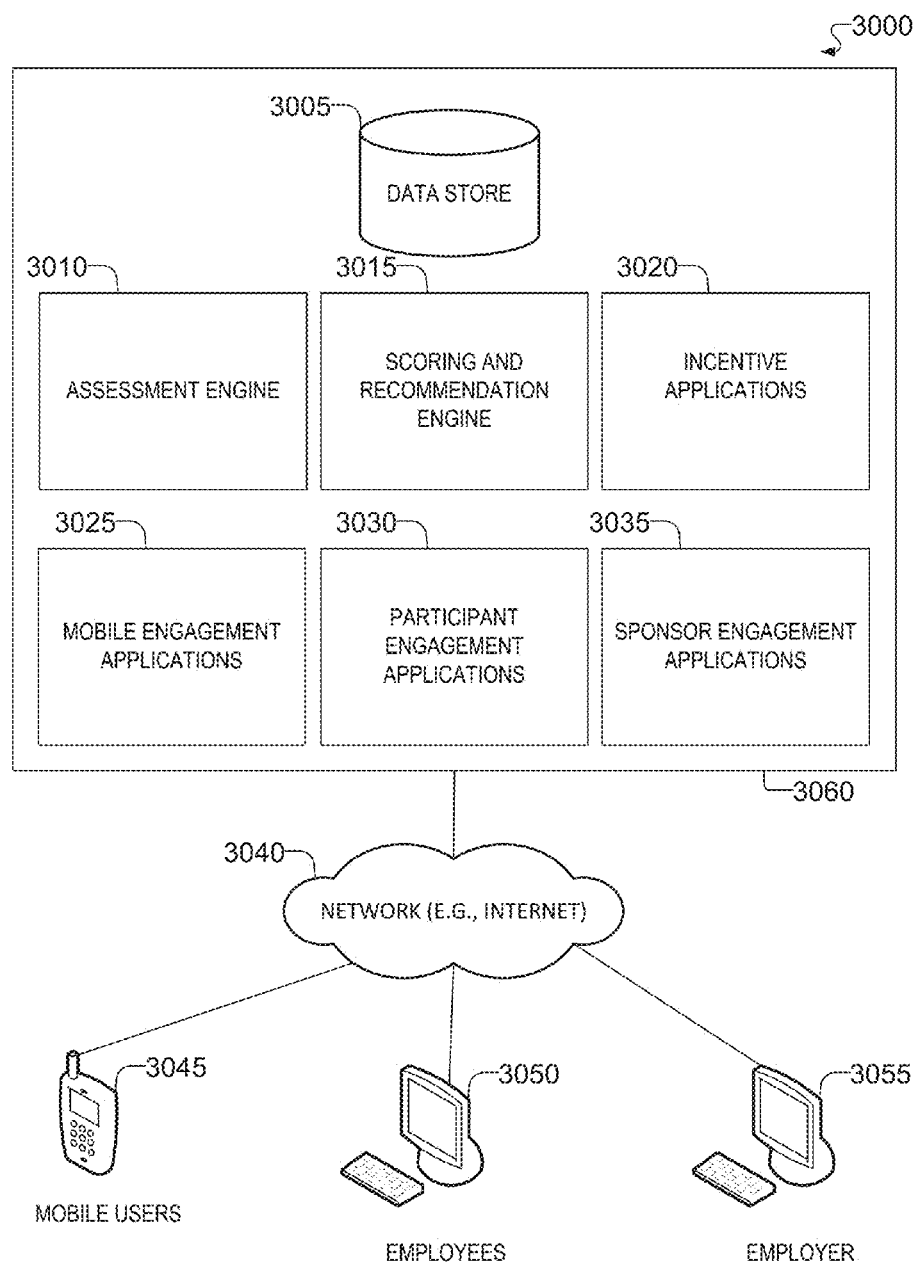
FIG. 3 shows a schematic of a wellness system according to some examples of the present disclosure.

FIG. 3 shows a wellness system 3000 according to some examples of the present disclosure. The wellness system 3000 may include one or more data stores 3005 (e.g., a database or other storage), an assessment engine 3010, a scoring and recommendation engine 3015, incentive applications 3020, mobile engagement applications 3025, employee engagement applications 3030, and employer engagement applications 3035. The data store 3005 may be used to store assessments, scores, recommendations, rules, and the like.

The assessment engine 3010 may receive assessment data from individuals, formulate the assessment presentations (e.g., through the employee engagement applications 3030, the mobile engagement applications 3025, and/or the employment engagement applications 3035), and store the assessment results in the data store 3005.

The scoring and recommendation engine 3015 may generate the scores for the wellness indicators based upon the assessment results and store the scores for the indicators in the data store 3005. As already noted, each question of an assessment may have a corresponding point value assigned to a particular answer. Point values from one or more questions may be combined and weighted to produce a particular indicator. A particular indicator may use the results from one or more question to arrive at the value for that indicator, and likewise, a particular question may be used in more than one indicator. Scoring and recommendation engine 3015 may also aggregate the indicators across a particular organizational level.

The scoring and recommendation engine 3015 may also generate the health component scores from the indicators as already noted. The scoring and recommendation engine 3015 may use a weighted sum of one or more of the indicators, weighted average of one or more of the indicators, or the like. A particular indicator may be used in the calculation of more than one component score. One or more of the indicators used in the calculations may be aggregated wellness indicators.

Scoring and recommendation engine 3015 may also calculate a total wellness score based upon the indicators, the component scores, or a combination of both. For example, the wellness score may be calculated using a weighted sum of one or more of the indicators and/or component scores, a weighted average of one or more of the indicators and/or component scores, or some other algorithm. One or more of the indicators used in the calculations may be aggregated indicators.

The scoring and recommendation engine 3015 may generate recommendations for an individual based upon the set of predetermined rules (which may be stored in the data store 3005). The scoring and recommendation engine 3015 may determine the list of groups that a participant is associated with (e.g., employer, family, industry, and the like) and the health group they are a part of (e.g., group 1, a healthy individual, group 2—an at risk individual, or group 3 an unhealthy individual) and based upon that information may retrieve the applicable set of predetermined recommendation rules. The scoring and recommendation engine 3015 may also retrieve another set of rules describing how to resolve conflicts (e.g., the priority) of the different rule sets. Based upon the rule sets, the conflict rules, and the individual's indicators (which may be aggregate indicators), component health scores, and total wellness score, the system may determine one or more recommendations to present to the participant.

The system may communicate these recommendations (as well as other health related and health insurance related information) via one or more engagement portals or platforms. Participant engagement applications or platforms 3030 may provide one or more internet web pages (e.g., a web site) for access by participants 3050 (or mobile users 3045 using a web browser). In the alternative, the engagement applications or platforms 3030 may provide application data and may communicate with a dedicated application on participant's computing device 3050. Mobile engagement applications 3025 may provide a mobile optimized version of the web pages (e.g., a web site) or may provide data for a mobile application running on mobile device 3045.

The engagement platforms may provide a user with tools to manage their program. The engagement platforms may allow for the administration and taking of assessments, provision for scoring the assessments, providing scores, wellness indicators, total wellness scores, health component scores, videos, tips, provide recommendations to the user, interfaces for reporting activities, and the like. The provided recommendations may be time based, location based, or the like. For example, if the system recommends a particular activity at a particular location or time of day, the engagement applications or platforms 3025-3030 may communicate this to the participant at the appropriate time or location.

The engagement platforms may interface with social networking sites (e.g., FACEBOOK®, LINKEDIN®), or include social components. For example, the engagement applications 3025-3030 may update a status on a social media portal with the improved wellness of the individual. The engagement applications may include social features that allow other participants, the public, or selected individuals to view an individual's health information.

The participant engagement applications 3030 may tailor the interaction between the participant and the sponsor-provided wellness system. For example, the engagement applications 3030 may provide a Personal Health Desktop to the participant. The sponsor (e.g., employer) engagement applications 3035 may tailor the interaction between the wellness administrator and the wellness system. For example, an Employer Health Desktop may allow a sponsor wellness administrator to view the progress of various participants, or view improvements in the overall wellness of a particular department and to view recommendations provided by the system for the sponsor (e.g., the employer).

The various components of the wellness system 3000 may be connected by a network (e.g., the internet) 3040 that connects the various components of the wellness infrastructure 3060 to mobile users 3045, employees 3050, or the employer 3055. For example, the mobile engagement applications 3025 may connect through the network 3040 to a participant's business or personal mobile device 3045, and allow the user to interact with the wellness system. Similarly, the engagement applications 3030 may connect through the network 3040 to participants 3050, or the engagement applications 3035 may connect through the network 3040 to participants 3055. The network 3040 may be or include portions of a cellular network, the Internet, a Wide Area Network (WAN), a Local Area Network (LAN), a corporate Intranet, or the like.

The incentive applications 3020 may calculate and apply incentives earned by the participants. The incentive applications 3020 may also reimburse the participant for activities engaged in. For example, the engagement applications may feature a rewards program whereby a cash reward is deposited to a participant's account, a Health Reimbursement Account (HRA) reimbursement or distribution is made, or the like.

Figure 4:
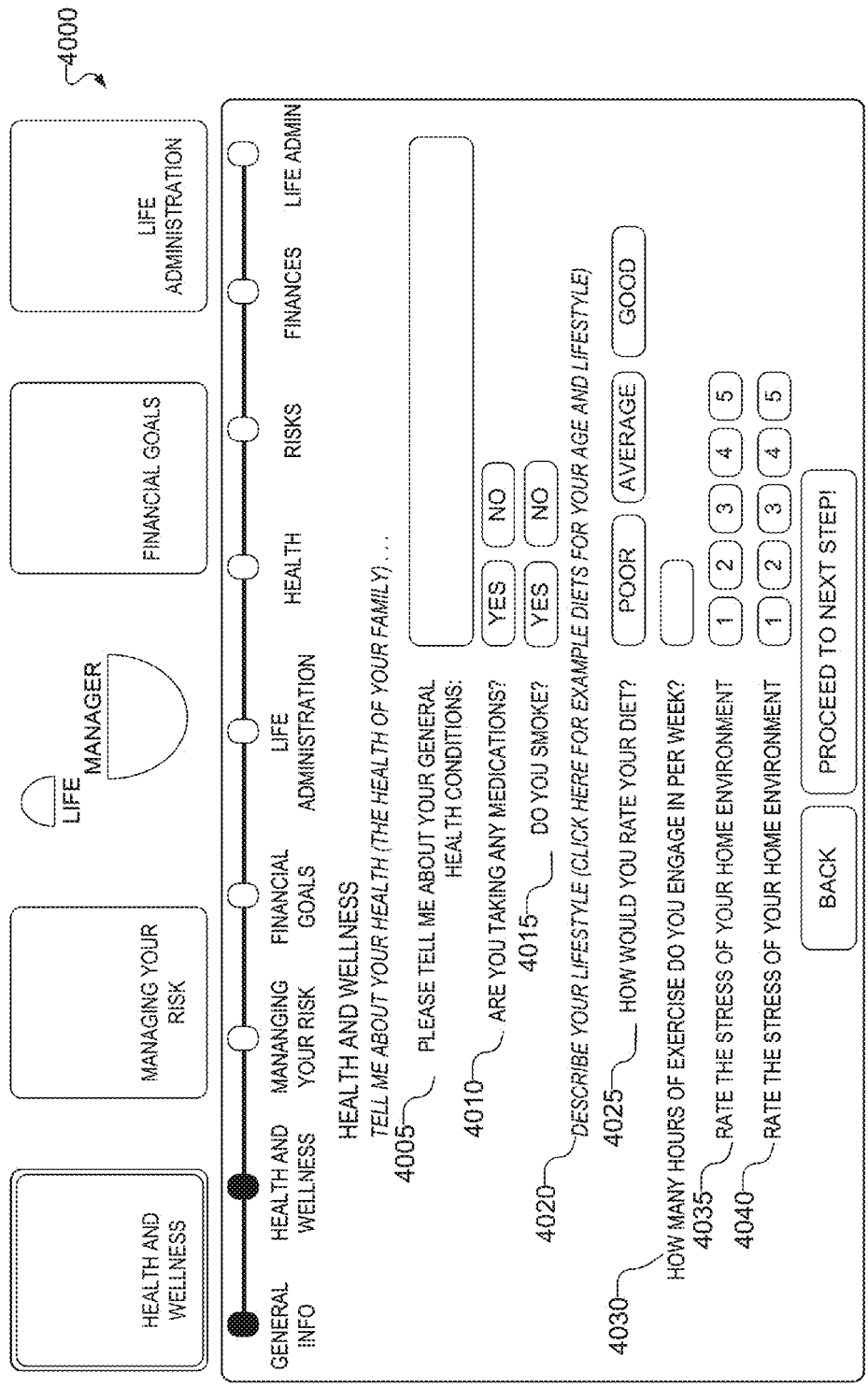
FIG. 4 shows a health and wellness questionnaire according to some examples of the present disclosure.

FIG. 4 shows a health and wellness questionnaire 4000 according to some examples of the present disclosure. The health and wellness questionnaire 4000 may prompt the user to list known health conditions 4005. The individual may be asked yes/no questions, including whether the individual is currently taking any medications 4010 or whether the individual smokes 4015. The individual may be prompted to click a link for example diets 4020, and then to rate the individual's diet either poor, average, or good 4025. The individual may be prompted to enter a number of hours of exercise per week 4030. The individual may be prompted to use a scale from one to five to rate the stress of the individual's work environment 4035 and the individual's home environment 4040.

Figure 5:
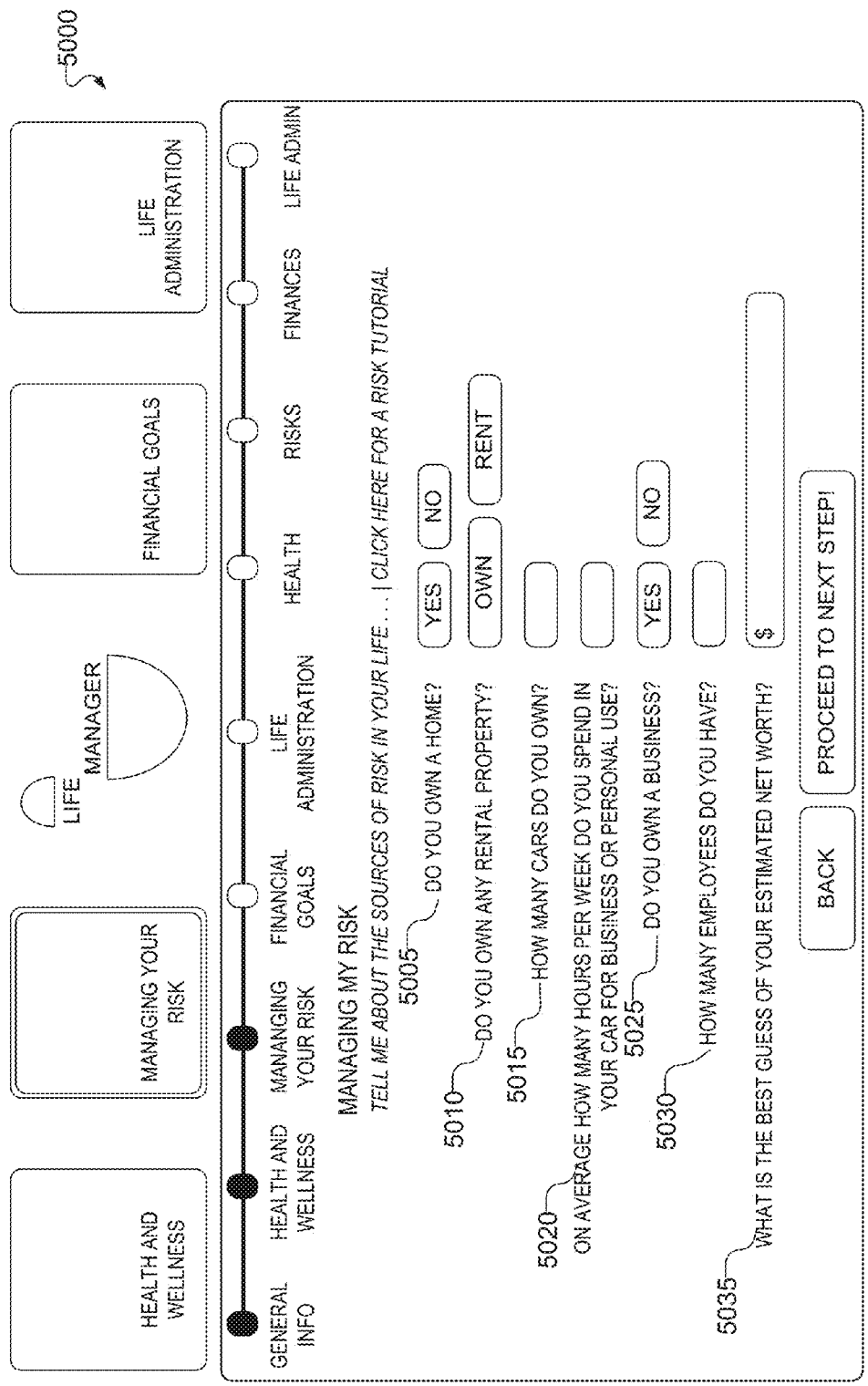
FIG. 5 shows a risk management questionnaire according to some examples of the present disclosure.

FIG. 5 shows a risk management questionnaire 5000 according to some examples of the present disclosure. The individual may be asked whether he or she owns a home 5005, or whether he or she owns or rents their house 5010. The individual may be prompted to enter a number of cars owned 5015. The individual may be prompted to enter an average number of hours per week spent in a car 5020. The individual may be asked whether he or she owns a business 5025, and if so, how many employees are employed by the business 5030. The individual may also be prompted to enter an estimate of net worth 5035.

Figure 6:
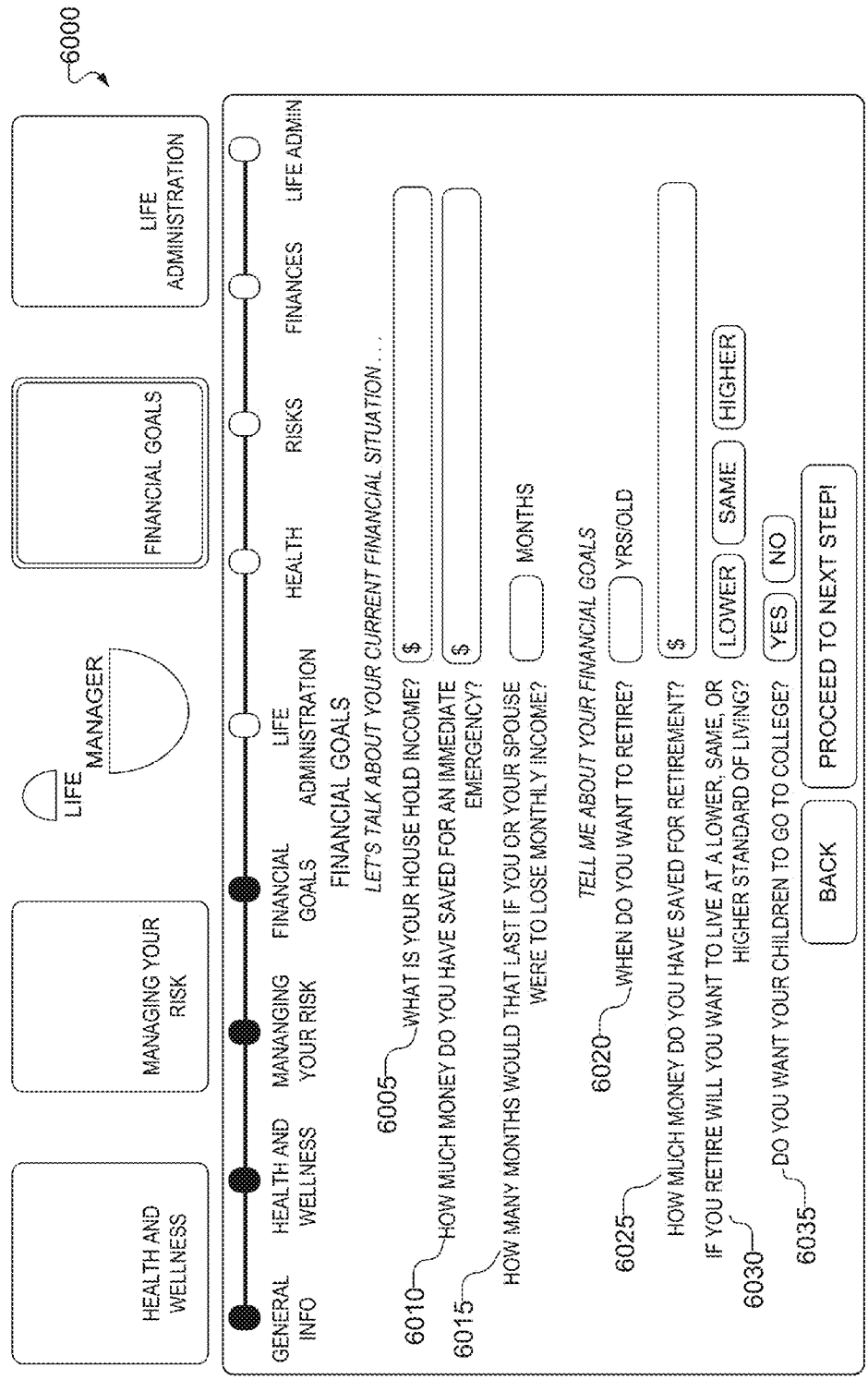
FIG. 6 shows a financial goal questionnaire according to some examples of the present disclosure.

FIG. 6 shows a financial goal questionnaire 6000 according to some examples of the present disclosure. The individual may be prompted to enter household income 6005. The individual may be prompted to enter how much money is currently saved for an immediate emergency 6010, or how many months the immediate emergency money would last if the individual or the individual's spouse lost their job 6015. The individual may be prompted to enter the age the individual wants to retire 6020, how much money the individual has already saved for retirement 6025, or whether the individual wants to retire at a higher or lower standard of living at retirement 6030. The individual may also be asked whether he or she plans to pay for their children's college education 6035.

Figure 7:
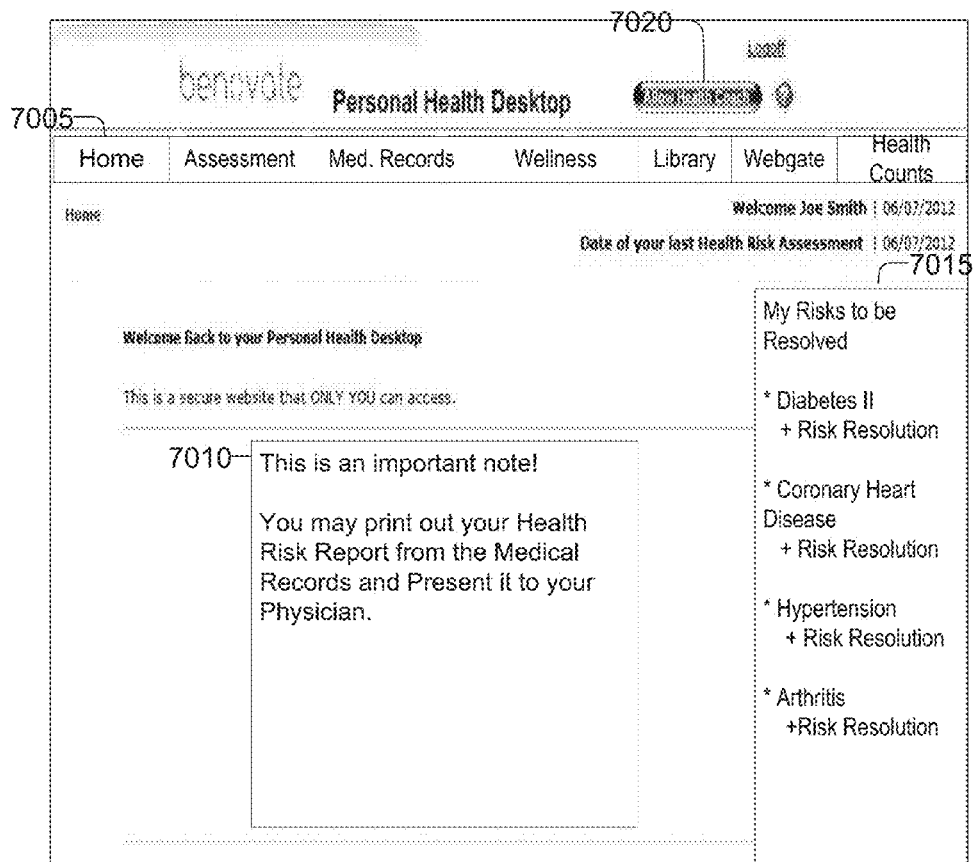
FIG. 7 shows a personal health desktop according to some examples of the present disclosure.

FIG. 7 shows a personal health desktop 7000 according to some examples of the present disclosure. The personal health desktop 7000 may include access to a series of personalized pages separated by tabs 7005. For example, pages may include a Home page, an Assessment page, a Medical Records page, a Wellness page, a Library page, a Health Webgate page, or a Health Counts page. The Home page may be the first page shown to the participant, and may include new or recently changed information aggregated from other pages. For example, the home page may include a notice or disclaimer 7010. The home page may also include a personalized list of risks and suggested risk resolution recommendations 7015, where clicking a hyperlink associated with a risk or resolution may open a new window or expand to display additional information. By accessing other personalized pages, individuals can access online Health Risk Reports, Health Library, Health Webgate, Risk Resolution Guidelines, and Vital Statistics Trackers. Individuals may also access health-related videos and use many other tools to maintain and improve their personal health. The personal health desktop 7000 may also include a link on all pages to grant access to the individual's Health Coach. For example, a Health Coach may be granted access to all of the pages available in an individual's personal health desktop 7000, and may work with the individual to create and maintain a personalized health care plan.

Figure 8:
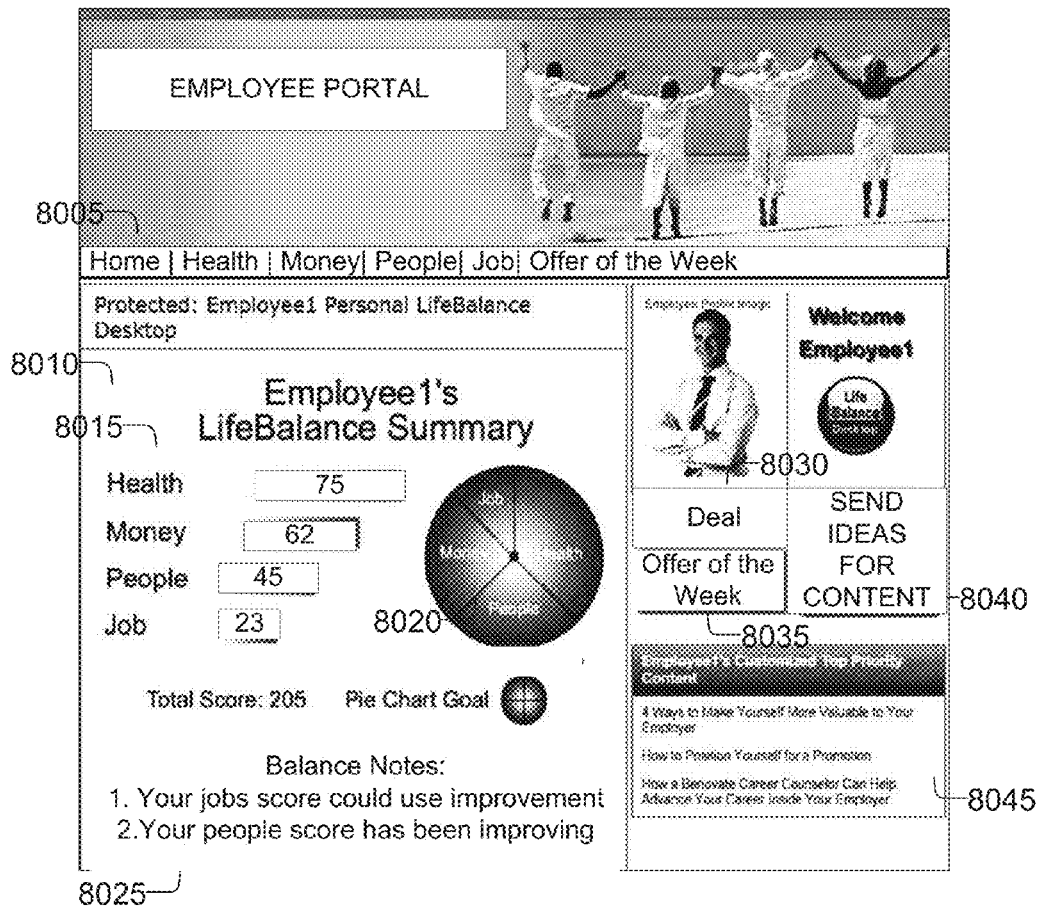
FIG. 8 shows a LifeBalance Desktop according to some examples of the present disclosure.

FIG. 8 shows a LifeBalance Desktop 8000 according to some examples of the present disclosure. The LifeBalance Desktop 8000 may include access to a series of personalized pages accessible by clicking hyperlinks 8005. For example, pages may include a Home page, a Health page, a Money page, a People page, a Job page, or an Offer of the Week page. The Home page may be the first page shown to the participant, and may include new or recently changed information aggregated from other pages. For example, the home page may include a LifeBalance Summary 8010. The LifeBalance Summary 8010 may include individual scores for various categories 8015, including Health, Money, People, or Job. The scores may represent a value between one and one hundred, where higher scores represent better health than lower scores.

To encourage individuals to balance each of the categories, the category scores may be included on a pie chart 8020. The pie chart can help an individual visualize when one category is significantly larger than another category. For example, a health score of seventy-five and a job score of twenty-three may indicate an individual should focus on improving his or her career score. To correct a score imbalance, one or more Balance Notes 8025 may be included. For example, Balance Notes 8025 may identify the lowest score and provide recommendations for improving the score. Balance Notes 8025 may provide ongoing information about category score trends, such as which category scores have been increasing. Balance Notes 8025 may also provide encouragement for consistently high scores, and recommendations for keeping the score high.

The home page may include options to increase participation. For example, an individual may be prompted to unlock an offer by completing one or more actions 8030, or may be prompted to click for a personalized offer of the week 8035. An individual may also send content suggestions for future health video episodes 8040. The home page may include a customized list of top priority content 8045, where the top priority content 8045 may include hyperlinked articles that provide recommendations for improving one or more of the categories that have low scores. For example, if a job score is twenty-three, the top priority content 8045 may include articles for becoming more valuable to an employer, positioning for a promotion, or contacting a career counselor.

Figure 9:
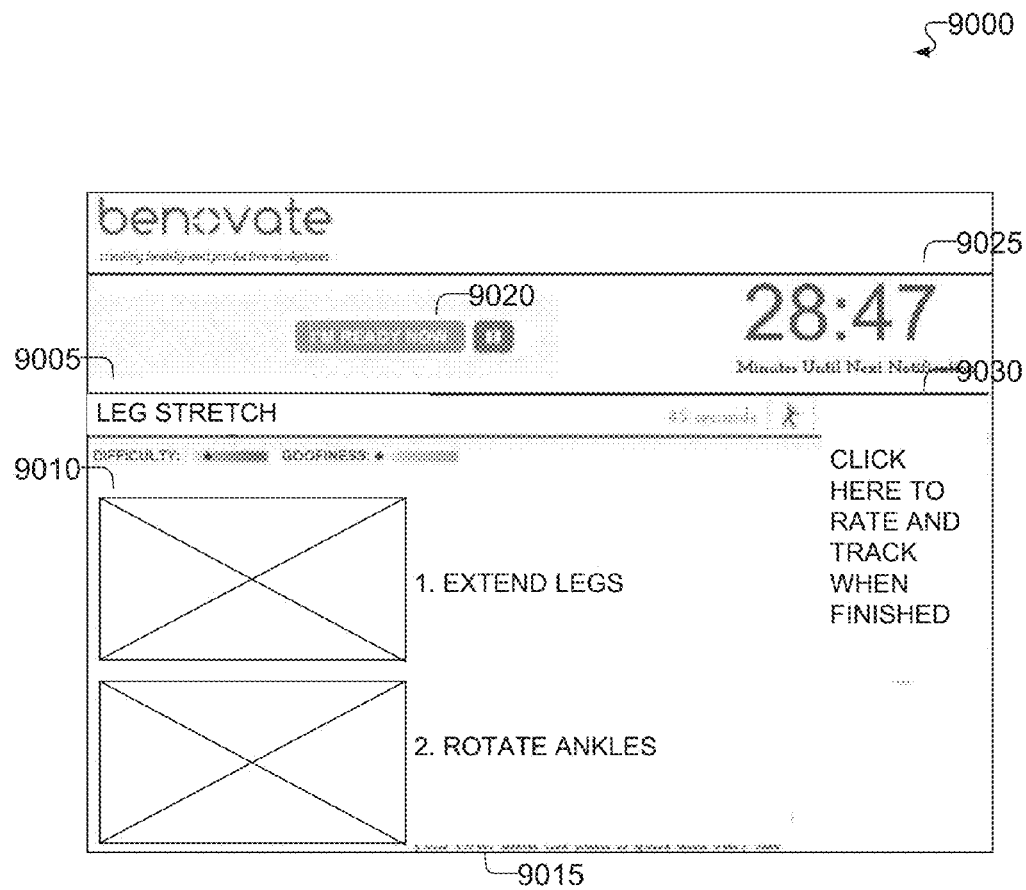
FIG. 9 shows a sample recommendation according to some examples of the present disclosure.

FIG. 9 shows a sample recommendation 9000 according to some examples of the present disclosure. A sample recommendation 9000 may include a recommendation title and general recommendation information 9005. To explain the steps required to execute the recommendation, a series of photographs may be provided 9010, where each photo has an accompanying textual description 9015. A recommendation demonstration video may be provided, and may be played and stopped using provided video controls 9020.

The recommendation page may include a timer 9025 that counts down the time until the next recommendation is provided. The time provided for executing a recommendation may be adjusted according to the duration of the recommendation, such as providing thirty minutes to execute a forty-five second recommendation. The time provided for executing a recommendation may be adjusted according to the purpose and intensity of individual's goals. For example, if an individual has an aggressive goal to improve health, the timer might provide a short amount of time between execution of each required recommendation. To encourage reporting execution of recommendations, the recommendation page may include a rating and tracking banner 9030. The banner may include a simplified rating system, such as a thumbs-up or thumbs-down recommendation. The banner may include a simplified track button, where clicking the track button indicates the user has executed the recommendation. The banner may also include an option to indicate a positive experience while executing the recommendation. For example, if executing a recommendation immediately improved how an individual is feeling, he or she may indicate a positive experience by clicking a star icon. Based on the type of recommendations that correspond to a positive experience, future recommendations may be provided that are of the same type. For example, if an individual indicated a positive experience during a back stretching exercise, future recommendations may be chosen according to whether they include a stretching component.

EXAMPLES

Turning now to FIG. 11, an example of a portion of a personal stress survey is shown. In the example of FIG. 11, financial stress questions are presented. These questions—with answer choices in parenthesis include:

What is your household income? (free text entry)

I have a lot of stress around paying my monthly bills (strongly disagree, disagree, in between, agree, strongly agree).

I need the following to pay my bills and save 20% of my income (40% more, 20% more, I have enough, 20% less, 40% less).

How much do you have saved for an emergency? (free text entry)

How many months could you survive without income? (6 months, 3 months, 2 months, 1 month, none).

In how many years do you want to retire (30+, 20+, 15+, 10+, <5).

How much money do you have saved for retirement? (free text entry).

At retirement what standard of living are you planning on? (much less, less, same, higher, much higher).

Do you want your children to go to college? (No, If its affordable, yes, it's a priority, its required).

I am very concerned about saving money (strongly disagree, disagree, in between, agree, strongly agree).

I pay my bills consistently on the same day each month (strongly disagree, disagree, in between, agree, strongly agree).

I do a personal budget for me and/or my family each: (<3 months, <6 months, <12 months, <2 years, never).

I meet with my financial planner ever (2+ years, 12 months, 6 months, 3 months, none).

I update my will or death plan every (2+ years, 12 months, 6 months, 3 months, none).

I have enough saved for life insurance to support my family or loved ones for the following time period (30+, 20+, 15+, 10+, <5).

If I am disabled my standard of living will be (much less, less, same, higher, much higher).

I am concerned about my loved one's ability to survive financially without my income (strongly disagree, disagree, in between, agree, strongly agree).

I am very concerned about my ability to retire (strongly disagree, disagree, in between, agree, strongly agree).

I have the ability to manage my finances on my own (strongly disagree, disagree, in between, agree, strongly agree).

I have a plan for where I will live when I am older (strongly disagree, disagree, in between, agree, strongly agree).

Each of these answers has a particular point rating (e.g., health event rating) of 1-4 as shown at 1110. Thus, if the participant answers the second question ("I have a lot of stress around paying my monthly bills.") as Strongly Agree, then that answer counts as 5 points times the multiplier 1120 for each health indicator 1130 ("Budget," "Debt," "Savings," "Investing," "Retirement," "Legacy") to which the question applies. For example, the second question counts towards the "Budget" health indicator. In this case the multiplier may be 5.5 (other multipliers may be utilized). Note that a multiplier may be negative. The totals for the health indicators are summed (e.g., in the Example of FIG. 11, the Budget total would be the sum of 22, −10, −27, 34). Note that, while the other health indicators are left blank, this is only to keep the example simple. One of ordinary skill in the art with the benefit of Applicant's disclosure will appreciate that the other health indicators would be calculated similarly. All the health indicators may then be weighted and summed to produce a component score for money stresses (e.g., financial health stress) of 13—which is "at risk." This shows one example for one aspect of the survey process. Again, one of ordinary skill in the art would appreciate that other surveys may employ similar processes.

In some examples, the questions asked during the survey may change depending on previous answers. Thus if a person's reported income is high enough, future questions may focus less on paying off bills and more on financial planning aspects. This may be accomplished using a script that specifies a flowchart for a particular survey and the next question to ask based upon specific answers.

Other health component scores may be calculated in the same or similar way. FIG. 12 demonstrates a sample of health risk scoring using 4 health component scores (financial (money), relationships (people), career (job), and health). Once each component score is calculated, each component may be prioritized based upon the perceived risk. In this example, the financial component is deemed to be most at risk, followed by relationships (people) scores, job scores, and health scores.

Based upon the prioritized components, the particular groups the participant is a part of, and the like, the system may recommend healthy activities for the user. In some examples, the activities recommended may include those in the prioritized health component categories. For example, the financial health component.

Figure 13:
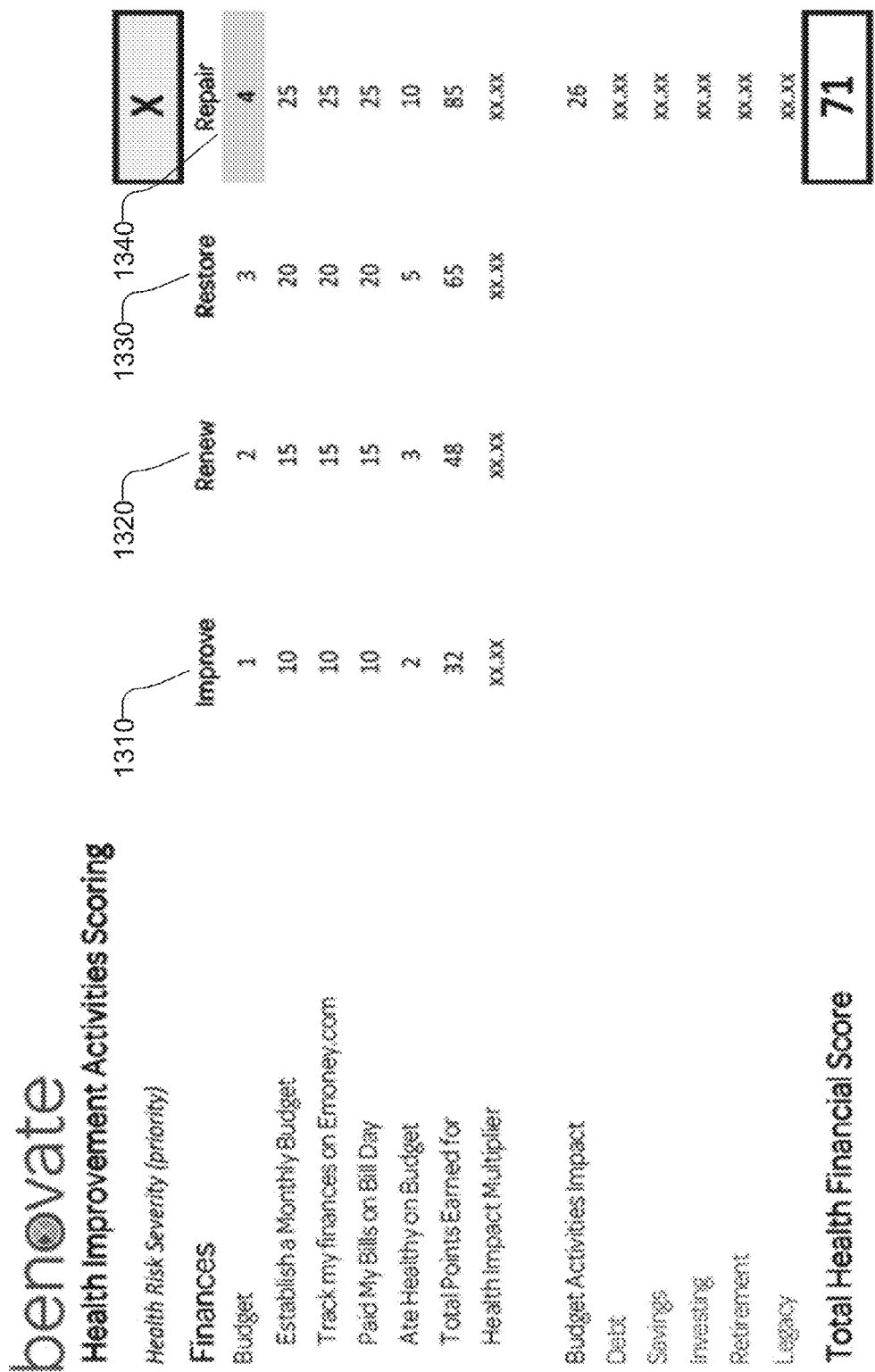
FIG. 13 shows a scoring chart of example activities according to some examples of the present disclosure.

FIG. 13 shows a sampling of activities to earn points towards improve the financial health score (and thus overall score as the financial health score may be a component of the overall score). For example, participants may be categorized within each health component as needing improvement 1310, needing renewal 1320, needing restoration 1330 and needing repair 1340. How badly improvement is needed increases from improvement 1310 to repair 1340. In this example, the participant needs serious help and is categorized in the "repair" category. In the Figure, various point values are awarded to each task ("establish a monthly budget, track my finances," "paid my bills on bill day," "ate healthy on budget," and others) based upon the category the participant falls under. For example, if the participant shown in FIG. 13 established a monthly budget, they would get 25 points. This would get multiplied by a multiplier (e.g., 0.75) to determine a point total for the budget indicator. If the participant in FIG. 13 did all the activities shown, they could earn a maximum of 26 points for budget activities. In the example shown in FIG. 13, the other health indicators (debt, savings, investment, retirement, legacy) may also have similar tables showing activities for improvement. Those may also impact the score as well. Thus if the participant did all the activities for all the various indicators, they would earn 71 points towards improving their financial health component. Note that this is not an increase in, or an increase to 71 for the financial health component (e.g., the money component), but a point total to be applied towards increasing the health component score as will be shown in FIG. 14.

Figure 14:
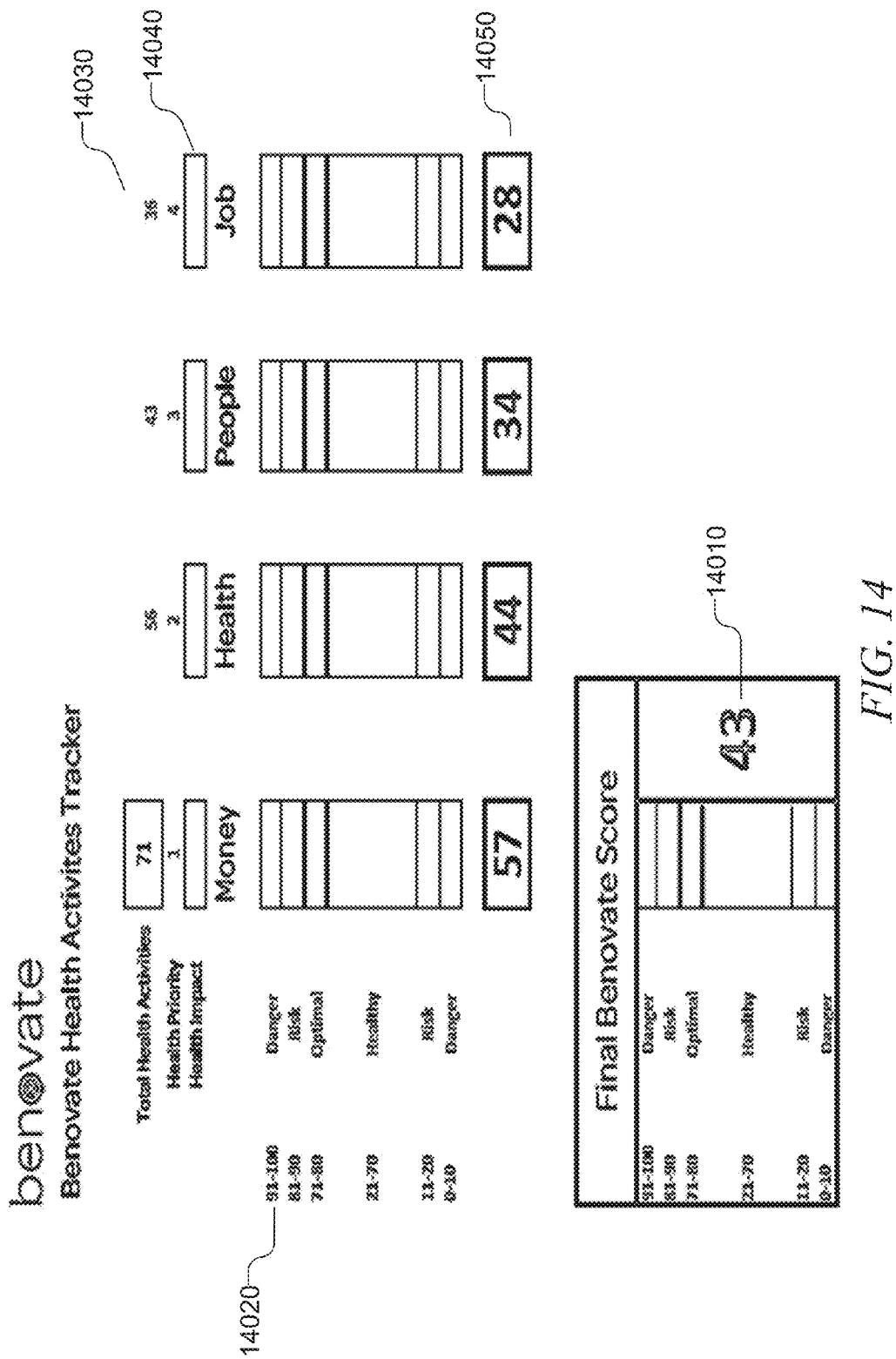
FIG. 14 shows a scoring chart for calculating a final score according to some examples of the present disclosure.

FIG. 14 shows an example of how healthy activities increase or decrease a final score. FIG. 14 demonstrates how changes to the individual indicators based upon points earned impacts the total final wellness score 14010. Each score has a scale at the left hand side 14020 which describes that 71-80 is optimal, 21-70 is healthy, 11-20 and 81-90 is at risk, and 91-100 and 0-10 is dangerous (these are just examples, other ranges and classifications may be used). Note that, 75 may be the optimal score in some examples, as some stress may be healthy, thus 100, showing no stress may not be optimal.

The total points earned for each of the health components are shown across the top at 14030 (71 for money activities, 56 for health, 43 for people, 36 for job). Note that some activities may give participants points in multiple health indicators. The health impact points may be weighted by a weighting factor 14040 (the weightings are not shown in FIG. 14, but an example weighting may be around 0.75-

0.85—which may be based upon health priority) to produce a contribution for those activities to a final score for each component 14050. Thus by earning 71 points in the money component, the participant improved their money score to 57. The final score may then weight those components (in some examples the weighting may take into account the health priority) to come up with final score 14010.

Figure 15:
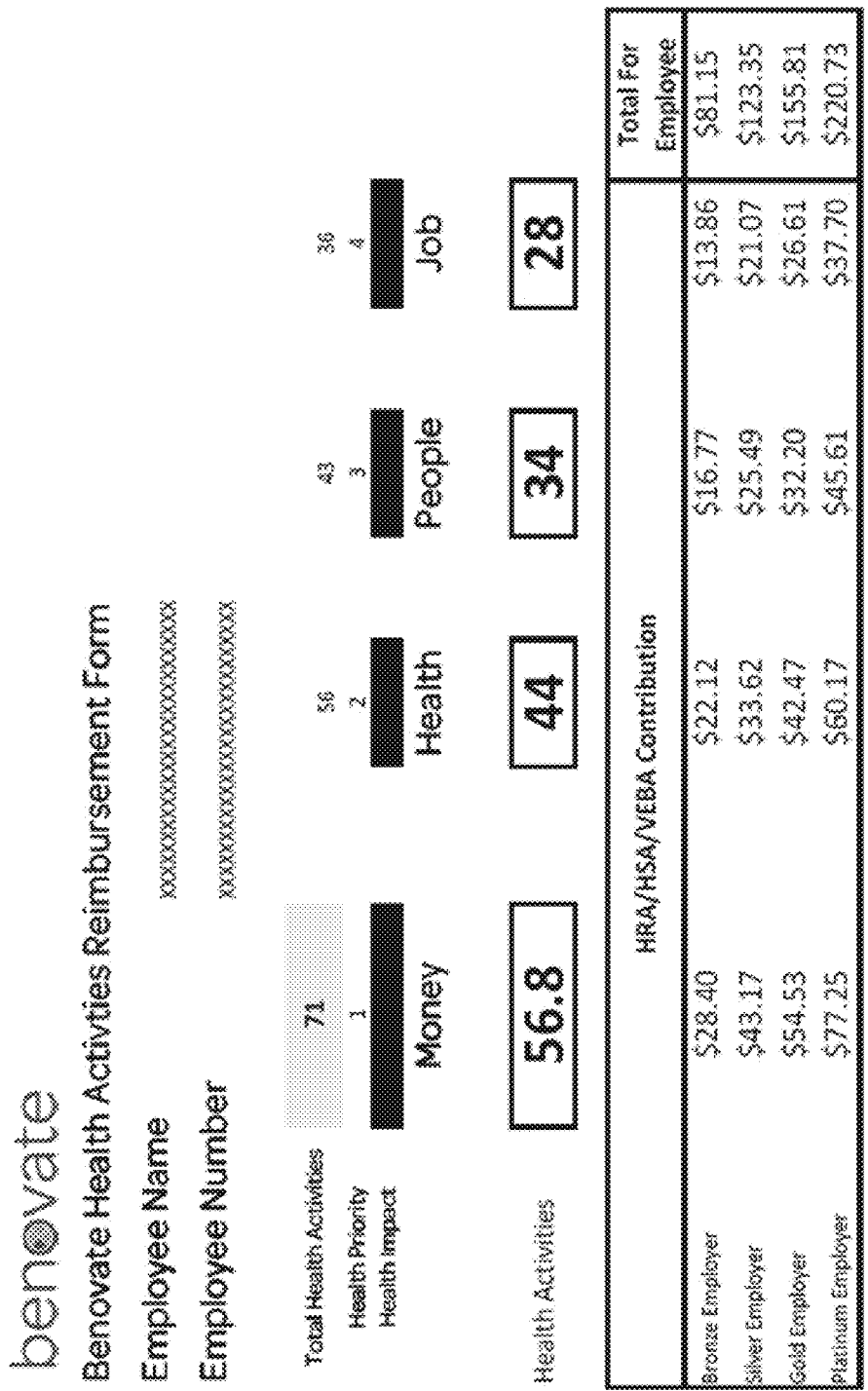
FIG. 15 shows an example of a health reimbursement according to some examples of the present disclosure.

FIG. 15 shows one example of employer reimbursements. For example, depending on the number of health activities and the level of employer (bronze, silver, gold, platinum) the employees may be compensated in the form of one or more of an Health Reimbursement Account (HRA), Health Savings Account, Voluntary Employee Beneficiary Association, or other compensation.

Modules, Components and Logic

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., APIs).

Electronic Apparatus and System

Example embodiments may be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 10:
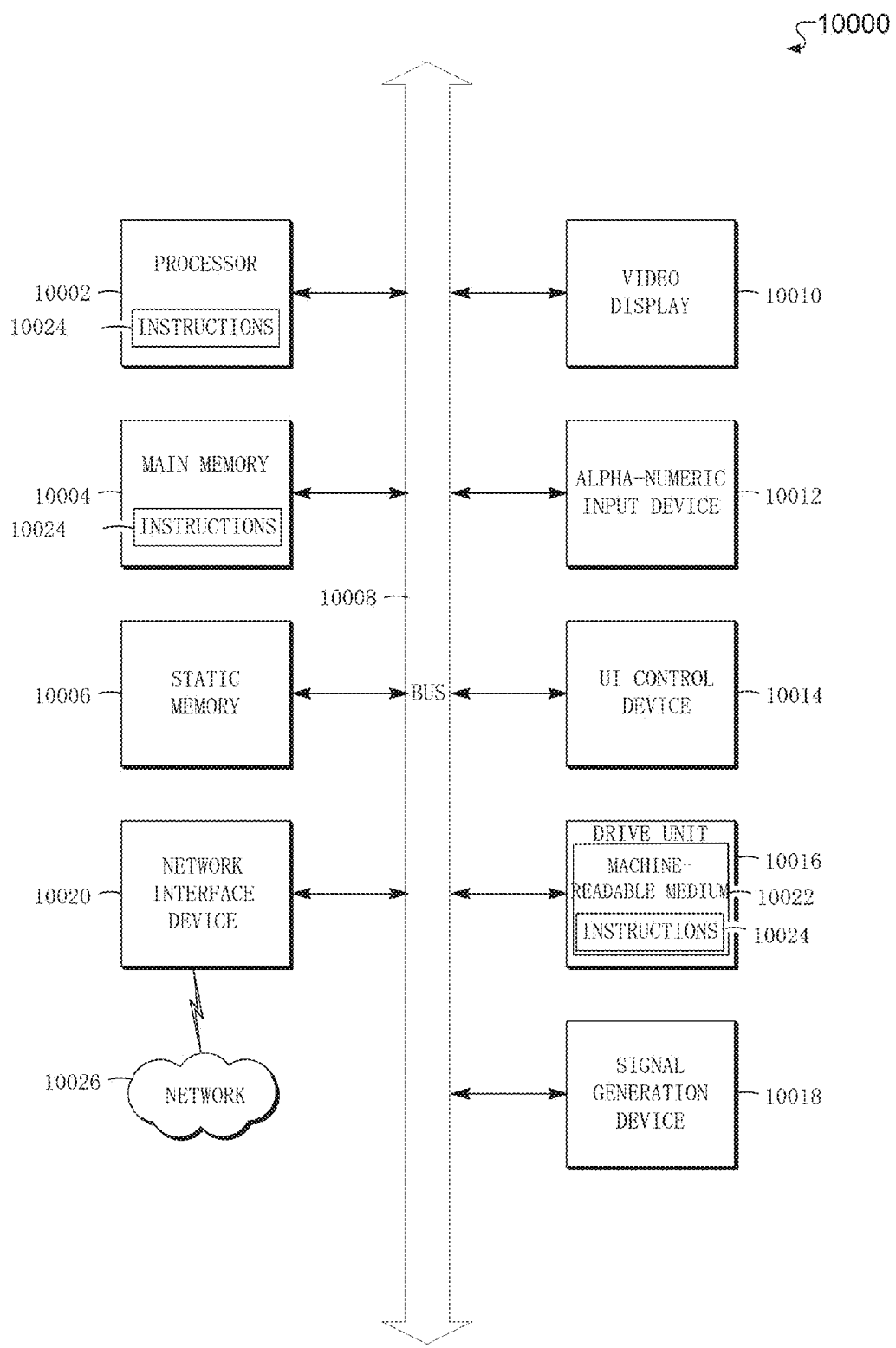
FIG. 10 shows a schematic of a machine according to some examples of the present disclosure.

FIG. 10 is a block diagram of machine in the example form of a computer system 10000 within which instructions, for causing the machine to perform any one or more of the methodologies discussed herein, may be executed. For example, any one of the components shown in FIG. 3 may be or contain one or more of the components described in FIG. 7. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a notebook PC, a docking station, a wireless access point, a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. The machine may contain components not shown in FIG. 7 or only a subset of the components shown in FIG. 7.

The example computer system 10000 includes a processor 10002 (e.g., a central processing unit (CPU), a graphics processing unit (GPU) or both), a main memory 10004 and a static memory 10006, which communicate with each other via a bus 10008. The computer system 10000 may further include a video display unit 10010 (e.g., a liquid crystal display (LCD) or a cathode ray tube (CRT)). The computer system 10000 also includes an alphanumeric input device 10012 (e.g., a keyboard), a user interface (UI) navigation device 10014 (e.g., a mouse), a disk drive unit 10016, a signal generation device 10018 (e.g., a speaker) and a network interface device 10020.

Machine-Readable Medium

The disk drive unit 10016 includes a machine-readable medium 10022 on which is stored one or more sets of instructions and data structures (e.g., software) 10024 embodying or used by any one or more of the methodologies or functions described herein. The instructions 10024 may also reside, completely or at least partially, within the main memory 10004, static memory 10006, and/or within the processor 10002 during execution thereof by the computer system 10000, the main memory 10004 and the processor 10002 also constituting machine-readable media.

While the machine-readable medium 10022 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., Erasable Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

Transmission Medium

The instructions 10024 may further be transmitted or received over a communications network 10026 using a transmission medium. The instructions 10024 may be transmitted using the network interface device 10020 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software. Network interface 10020 may wirelessly transmit data and may include an antenna.

Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

OTHER EXAMPLES

The following are non-limiting examples of the present disclosure.

Example 1

A computer-implemented method including using one or more computer processors to perform the operations of: receiving responses for a plurality of assessments for an individual, the responses including responses for assessments of at least one physical and at least one psychological component of the individual's wellness; calculating numerical indicators for a plurality of wellness indicators for the individual based on the plurality of responses; determining at least one set of rules based upon at least one organization that the individual is associated with; determining a wellness recommendation based upon the set of rules and the numerical indicators; and presenting the wellness recommendation to the individual.

Example 2

The method of example 1, wherein the method further comprises: aggregating the wellness indicators for the assessments of the plurality of assessments directed towards assessing an environment comprised of a plurality of participants which includes the individual, and wherein the wellness recommendation is based upon the aggregated wellness indicators for those assessments.

Example 3

The method of any one of examples 1-2, wherein the method further comprises calculating a plurality of wellness components.

Example 4

The method of example 3, wherein the wellness components include at least two of: a health component, a money stress component, a people component, and a jobs component.

Example 5

The method of example 4, wherein the method further comprises: calculating an overall wellness score based on the plurality of wellness components.

Example 6

The method of any one of examples 1-5, wherein the plurality of assessments comprise one of: culture, climate, relationship and family, money, and health assessments.

Example 7

The method of example 6, further comprising: receiving an indication that the individual participated in an activity associated with the wellness recommendation; and responsive to receiving the indication calculating a reward for the individual.

Example 8

The method of example 7, wherein the reward is a contribution to a Health Reimbursement Account (HRA).

Example 9

A system comprising: an assessment module configured to: receive responses for a plurality of assessments for an individual, the responses including responses for assessments of at least one physical and at least one psychological component of the individual's wellness; a scoring module configured to: calculate numerical indicators for a plurality of wellness indicators for the individual based on the plurality of responses; determine at least one set of rules based upon at least one organization that the individual is associated with; determine a wellness recommendation based upon the set of rules and the numerical indicators; and an engagement module configured to present the wellness recommendation to the individual.

Example 10

The system of example 9, wherein the scoring module is configured to: aggregate the wellness indicators for the assessments of the plurality of assessments directed towards assessing an environment comprised of a plurality of participants which includes the individual, and determine the wellness recommendation based upon the aggregated wellness indicators for those assessments.

Example 11

The system of any one of examples 9-10, wherein the scoring module is configured to calculate a plurality of wellness components.

Example 12

The system of example 11, wherein the wellness components include at least two of: a health component, a money stress component, a people component, and a jobs component.

Example 13

The system of example 12, wherein the scoring module is configured to calculate an overall wellness score based on the plurality of wellness components.

Example 14

The system of any one of examples 9-13, wherein the plurality of assessments comprise one of: culture, climate, relationship and family, money, and health assessments.

Example 15

The system of example 14, wherein the engagement module is configured to receive an indication that the individual participated in an activity associated with the wellness recommendation; and the system further comprises an incentive module configured to calculate a reward for the individual responsive to the engagement module receiving the indication.

Example 16

The system of example 15, wherein the reward is a contribution to a Health Reimbursement Account (HRA).

Example 17

A machine readable medium that stores instructions which when performed by a machine, cause the machine to perform operations comprising: receiving responses for a plurality of assessments for an individual, the responses including responses for assessments of at least one physical and at least one psychological component of the individual's wellness; calculating numerical indicators for a plurality of wellness indicators for the individual based on the plurality of responses; determining at least one set of rules based upon at least one organization that the individual is associated with; determining a wellness recommendation based upon the set of rules and the numerical indicators; and presenting the wellness recommendation to the individual.

Example 18

The machine readable medium of example 17, wherein the instructions further include instructions, which when performed by the machine, cause the machine to perform the operations comprising: aggregating the wellness indicators for the assessments of the plurality of assessments directed towards assessing an environment comprised of a plurality of participants which includes the individual, and wherein the wellness recommendation is based upon the aggregated wellness indicators for those assessments.

Example 19

The machine readable medium of any one of examples 17-18, wherein the instructions further include instructions, which when performed by the machine, cause the machine to perform the operations comprising calculating a plurality of wellness components.

Example 20

The machine readable medium of example 19, wherein the wellness components include at least two of: a health component, a money stress component, a people component, and a jobs component.

Example 21

The machine readable medium of example 20, wherein the instructions further include instructions, which when performed by the machine, cause the machine to perform the operations comprising calculating an overall wellness score based on the plurality of wellness components.

Example 22

The machine readable medium of any one of examples 17-20, wherein the plurality of assessments comprise one of: culture, climate, relationship and family, money, and health assessments.

Example 23

The machine readable medium of example 22, wherein the instructions further include instructions, which when performed by the machine, cause the machine to perform the operations comprising: receiving an indication that the individual participated in an activity associated with the wellness recommendation; and responsive to receiving the indication calculating a reward for the individual.

Example 24

The machine readable medium of example 23, wherein the reward is a contribution to a Health Reimbursement Account (HRA).

What is claimed is:

1. A computer-implemented method comprising:
using one or more computer processors to perform the operations of:
receiving responses for a plurality of assessments for an individual, the responses including responses for assessments of at least one physical and at least one psychological component of the individual's wellness;
calculating numerical indicators for a plurality of wellness indicators for the individual based on a predetermined set of weights applied to a point value for each of the plurality of responses;
determining at least one set of rules based upon at least one organization that the individual is associated with;
determining a wellness recommendation based upon the set of rules and the numerical indicators;
presenting the wellness recommendation to the individual via a mobile device;
verifying compliance with the wellness recommendation based on a mobile tracking device input received from a sensor of the mobile device;
providing a reward to the individual in response to verifying compliance with the wellness recommendation; and
presenting an indication of the reward to the individual via the mobile tracking device.

2. The method of claim 1, wherein the method further comprises:

aggregating the wellness indicators for the assessments of the plurality of assessments directed towards assessing an environment comprised of a plurality of participants which includes the individual, and wherein the wellness recommendation is based upon the aggregated wellness indicators for those assessments.

3. The method of claim 1, wherein the method further comprises calculating a plurality of wellness components.

4. The method of claim 3, wherein the wellness components include at least two of:

a health component, a money stress component, a people component, and a jobs component.

5. The method of claim 4, wherein the method further comprises:

calculating an overall wellness score based on the plurality of wellness components.

6. The method of claim 1, wherein the plurality of assessments comprise one of:

culture, climate, relationship and family, money, and health assessments.

7. The method of claim 6, wherein the mobile tracking device input includes at least one of a mobile device location or a mobile device motion.

8. The method of claim 7, wherein the reward is a contribution to a Health Reimbursement Account (HRA).

9. A system comprising:

a processor configured to execute instructions provided from a plurality of software modules, the plurality of software modules including:

an assessment software module configured to:

receive data associated with a plurality of responses for a plurality of assessments for an individual, the plurality of responses including responses for assessments of at least one physical and at least one psychological component of the individual's wellness:

a scoring software module configured to:

calculate numerical indicators for a plurality of wellness indicators for the individual based on a predetermined set of weights applied to a point value for each of the plurality of responses;

determine at least one set of rules based upon at least one organization that the individual is associated with;

determine a wellness recommendation based upon the set of rules and the numerical indicators; and an engagement software module configured to:

present the wellness recommendation to the individual via a mobile device;

verify compliance with the wellness recommendation based on a mobile tracking device input received from a sensor of the mobile device;

provide a reward to the individual in response to verifying compliance with the wellness recommendation; and present an indication of the reward to the individual via the mobile tracking device.

10. The system of claim 9, wherein the scoring software module is configured to:

aggregate the wellness indicators for the assessments of the plurality of assessments directed towards assessing an environment comprised of a plurality of participants which includes the individual, and determine the wellness recommendation based upon the aggregated wellness indicators for those assessments.

11. The system of claim 9, wherein the scoring software module is configured to calculate a plurality of wellness components.

12. The system of claim 11, wherein the wellness components include at least two of:

a health component, a money stress component, a people component, and a jobs component.

13. The system of claim 12, wherein the scoring software module is configured to calculate an overall wellness score based on the plurality of wellness components.

14. The system of claim 9, wherein the plurality of assessments comprise one of:

culture, climate, relationship and family, money, and health assessments.

15. The system of claim 14, wherein the indication includes at least one of a mobile device location or a mobile device motion.

16. The system of claim 15, wherein the reward is a contribution to a Health Reimbursement Account (LIRA).

17. A non-transitory machine readable medium that stores instructions which when performed by a machine, cause the machine to perform operations comprising:

receiving responses for a plurality of assessments for an individual, the responses including responses for assessments of at least one physical and at least one psychological component of the individual's wellness;

calculating numerical indicators for a plurality of wellness indicators for the individual based on a predetermined set of weights applied to a point value for each of the plurality of responses;

determining at least one set of rules based upon at least one organization that the individual is associated with;

determining a wellness recommendation based upon the set of rules and the numerical indicators;

presenting the wellness recommendation to the individual via a mobile device;

verifying compliance with the wellness recommendation based on a mobile tracking device input received from a sensor of the mobile device;

providing a reward to the individual in response to verifying compliance with the wellness recommendation; and presenting an indication of the reward to the individual via the mobile tracking device.

18. The non-transitory machine readable medium of claim 17, wherein the instructions further include instructions, which when performed by the machine, cause the machine to perform the operations comprising:

aggregating the wellness indicators for the assessments of the plurality of assessments directed towards assessing an environment comprised of a plurality of participants which includes the individual, and wherein the \wellness recommendation is based upon the aggregated wellness indicators for those assessments.

19. The non-transitory machine readable medium of claim 17, wherein the instructions further include instructions, which when performed by the machine, cause the machine to perform the operations comprising calculating a plurality of wellness components.

20. The non-transitory machine readable medium of claim 19, wherein the wellness components include at least two of:

a health component, a money stress component, a people component, and a jobs component.

21. The non-transitory machine readable medium of claim 20, wherein the instructions further include instructions, which when performed by the machine, cause the machine to perform the operations comprising calculating an overall wellness score based on the plurality of wellness components.

22. The non-transitory machine readable medium of claim 17, wherein the plurality of assessments comprise one of: culture, climate, relationship and family, money, and health assessments.

23. The non-transitory machine readable medium of claim 22, wherein the mobile tracking device input includes at least one of a mobile device location or a mobile device motion.

24. The non-transitory machine readable medium of claim 23, wherein the reward is a contribution to a Health Reimbursement Account (HRA).

* * * * *

UNITED STATES PATENT AND TRADEMARK OFFICE
CERTIFICATE OF CORRECTION

PATENT NO. : 9,727,885 B1
APPLICATION NO. : 13/906760
DATED : August 8, 2017
INVENTOR(S) : Mike Reier It is certified that error appears in the above-identified patent and that said Letters Patent is hereby corrected as shown below:

In the Specification

In Column 6, Line 50, after "condition", insert --.--

In Column 17, Line 44, delete "1110." and insert --11010.-- therefor

In Column 17, Line 47, delete "1120" and insert --11020-- therefor

In Column 17, Line 48, delete "1130" and insert --11030-- therefor

In the Claims

In Column 27, Line 10, in Claim 3, after "comprises", insert --:¶--

In Column 27, Line 37-38, in Claim 9, delete "wellness:" and insert --wellness;-- therefor In Column 28, Line 20, in Claim 18, delete "(LIRA)." and insert --(HRA).-- therefor In Column 28, Line 53-54, in Claim 18, delete "Wellness" and insert --wellness-- therefor Signed and Sealed this
Twenty-eighth Day of May, 2019

Andrei Iancu
*Director of the United States Patent and Trademark Office*